(12) United States Patent
Bonnet-Gonnet et al.

(10) Patent No.: US 8,481,019 B2
(45) Date of Patent: Jul. 9, 2013

(54) MODIFIED-RELEASE PARTICLES OF POLYELECTROLYTES AND PHARMACEUTICAL FORMULATIONS THEREOF

(75) Inventors: Cecile Bonnet-Gonnet, Lyons (FR); Frédéric Checot, Lyons (FR); You-Ping Chan, Ternay (FR); Olivier Breyne, Lyons (FR)

(73) Assignee: Flamel Technologies (FR)

( * ) Notice: Subject to any disclaimer, the term of this patent is extended or adjusted under 35 U.S.C. 154(b) by 1113 days.

(21) Appl. No.: 12/149,552

(22) Filed: May 5, 2008

(65) Prior Publication Data
US 2009/0011039 A1    Jan. 8, 2009

Related U.S. Application Data

(60) Provisional application No. 60/924,215, filed on May 3, 2007.

(30) Foreign Application Priority Data

May 3, 2007 (FR) ..................................... 07 03187

(51) Int. Cl.
*A61K 31/74*    (2006.01)
(52) U.S. Cl.
USPC ........ 424/78.17; 424/401; 530/300; 562/571; 562/573; 514/1; 514/964; 514/965
(58) Field of Classification Search
None
See application file for complete search history.

(56) References Cited

U.S. PATENT DOCUMENTS

| 6,630,171 | B1 | 10/2003 | Huille et al. | |
|---|---|---|---|---|
| 7,659,365 | B2 * | 2/2010 | Soula et al. | 530/324 |
| 2006/0099264 | A1 | 5/2006 | Chan et al. | |
| 2007/0010652 | A1 | 1/2007 | Angot et al. | |
| 2007/0196497 | A1 | 8/2007 | Pouliquen et al. | |
| 2007/0248686 | A1 | 10/2007 | Touraud et al. | |
| 2007/0265192 | A1 | 11/2007 | Soula et al. | |
| 2009/0012028 | A1 | 1/2009 | Chan et al. | |
| 2010/0034886 | A1 | 2/2010 | Soula et al. | |
| 2010/0098656 | A1 * | 4/2010 | Breyne et al. | 424/85.2 |
| 2011/0044930 | A1 * | 2/2011 | Soula et al. | 424/78.17 |

FOREIGN PATENT DOCUMENTS

| FR | 2 801 226 | 5/2001 |
|---|---|---|
| FR | 2 840 614 | 12/2003 |
| FR | 2 855 521 | 12/2004 |
| FR | 2 860 516 | 4/2005 |
| FR | 2 881 140 | * 7/2006 |
| FR | 2 892 725 | 5/2007 |
| FR | 2 915 748 | 5/2007 |
| WO | WO 00/30618 | 6/2000 |
| WO | WO 2005/051416 | 6/2005 |

OTHER PUBLICATIONS

Fuller, W. et al., "A Procedure for the Facile Synthesis of Amino-Acid N-Carboxyanhydrides," *Biopolymers*, 1976;15:1869-71.
Tomida et al., "Convenient Synthesis of High Molecular Weight Poly(succinimide) by Acid-Catalysed Polycondensation of L-aspartic Acid," *Polymer*, 1997; 38:4733-36.

* cited by examiner

*Primary Examiner* — Robert A Wax
*Assistant Examiner* — Jeffrey T Palenik
(74) *Attorney, Agent, or Firm* — Patton Boggs LLP

(57) ABSTRACT

The present invention relates to novel particles comprising polyelectrolyte polymers which are transporters of active principle (AP), in particular protein and peptide active principle, and to novel modified-release pharmaceutical formulations comprising said AP microparticles.
These novel particles loaded with AP release the AP over a prolonged period of time of several days, or even several weeks.
The invention relates, in a first aspect, to particles comprising:
  a) a first polyelectrolyte polymer (PE1) in a charged state, carrying side hydrophobic groups (GH), wherein said first polyelectrolyte polymer (PE1) can spontaneously form, in water, a colloidal solution of particles at least one pHm value of the pH of between 3 and 8;
  b) a second polyelectrolyte polymer (PE2) of opposite polarity to the first polyelectrolyte polymer (PE1), wherein said second polyelectrolyte polymer (PE2) forms, in water, a solution or a colloidal solution at said pHm value of the pH; and
  c) at least one active principle (AP) associated noncovalently with the particles of the colloidal solution of the first polyelectrolyte polymer (PE1);
wherein said particles are obtained by mixing, at a pH equal to pHm, the first polyelectrolyte polymer (PE1), in the form of a colloidal solution of particles associated with the active principle (AP), with the second polyelectrolyte polymer (PE2), in the form of a solution or colloidal solution.
The invention also relates to the process for the preparation of these particles, to a pharmaceutical formulation comprising such particles and to a process for the preparation of medicaments.

19 Claims, 1 Drawing Sheet

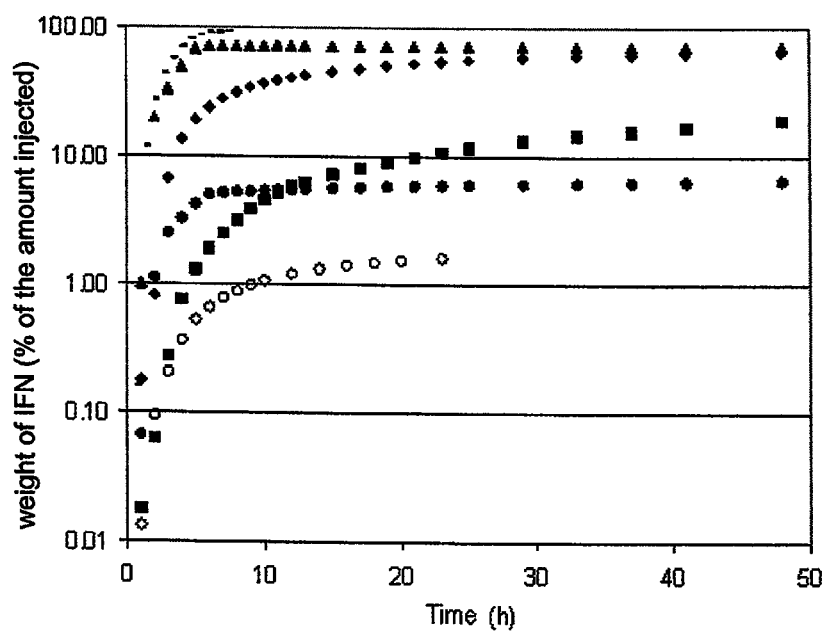

MODIFIED-RELEASE PARTICLES OF POLYELECTROLYTES AND PHARMACEUTICAL FORMULATIONS THEREOF

CROSS-REFERENCE TO RELATED APPLICATIONS

This application claims priority to French Application No. 0703187, filed May 3, 2007, currently pending and U.S. Provisional Application No. 60/924,215, filed May 3, 2007, currently pending. The contents of which are incorporated herein in their entirety.

FIELD OF THE INVENTION

The present invention relates to novel transporters of active principle(s) (AP), in particular protein and peptide active principle(s), and to novel modified-release pharmaceutical formulations comprising said AP transporters. The application also relates to the application or use, in particular therapeutic application or use of these pharmaceutical formulations. These active pharmaceutical formulations relate both to human therapeutics and veterinary therapeutics.

The term AP used throughout the present account refers to at least one active principle.

STATE OF THE ART

In the field of sustained release of pharmaceutical APs, in particular therapeutic peptides/proteins, the aim is very often to reproduce, as best as possible, in the patient a peptide or protein plasma concentration close to the value observed in healthy subjects.

This objective conflicts with the short lifetime of proteins in the plasma, which leads to repeated injections of the therapeutic protein. Consequently, the plasma concentration of a therapeutic protein exhibits a profile characterized by high concentration peaks and very low concentration minima. The concentration peaks, which are much higher than the basal concentration found in the healthy subject, have significant harmful effects to the high toxicity of therapeutic proteins such as cytokines. Furthermore, the concentration minima are below the concentration necessary to have a therapeutic effect, which results in poor therapeutic coverage of the patient and serious long-term side effects.

Consequently, in order to reproduce in the patient a plasma concentration of therapeutic protein close to the ideal value for treatment, it is important for the pharmaceutical formulation to allow the release of the therapeutic protein over a prolonged period of time, so as to limit the variations in plasma concentration over time.

Furthermore, this active formulation should preferably satisfy the following requirements, already known to a person skilled in the art:
1—sustained release of an active and nondenatured therapeutic protein, for example a human or synthetic protein, so that the plasma concentration is maintained at the therapeutic level;
2—sufficiently low viscosity at injection to be easily injectable;
3—biocompatible and biodegradable form exhibiting an excellent toxicity and tolerance profile.

In an attempt to achieve these objectives, one of the best approaches provided in the prior art was to develop sustained-release forms of therapeutic protein(s) composed of relatively nonviscous liquid suspensions of nanoparticles loaded with therapeutic proteins. These suspensions allow easy administration of native therapeutic proteins.

Thus, Flamel Technologies has provided a route in which the therapeutic protein is associated with nanoparticles of a copolyamino acid comprising hydrophobic groups and hydrophilic groups.

Patent application US 2006/0099264 discloses amphiphilic polyamino acids comprising aspartic residues and/or glutamic residues, wherein at least a portion of these residues carry grafts comprising at least one α-tocopherol residue, e.g.: (polyglutamate or polyaspartate grafted with α-tocopherol of synthetic or natural origin). These "hydrophobic modified" homopolyamino acids spontaneously form, in water, a colloidal suspension of nanoparticles which are capable of readily associate with at least one active protein (insulin) in an aqueous suspension at pH 7.4.

The in vivo release duration of the active protein(s) (e.g. insulin) "vectorized" by the suspensions described in US 2006/0099264 would benefit from being extended.

An increase in release duration was partially obtained using the pharmaceutical forms described in PCT application WO-A-05/051416. This application discloses a colloidal suspension of nanoparticles (0.001-0.5 μm) of hydrophobic modified poly(sodium L-glutamate) injected at a concentration such that, after subcutaneous injection, a gel is formed in situ in the patient on contact with endogenous albumin. The protein is then slowly released over a typical period of one week. However, when the concentration of therapeutic protein to be administered is relatively high, as is the case, for example, for human growth hormone, the release duration is limited to a few days.

The release duration of these forms would benefit from being further extended.

BRIEF DESCRIPTION OF THE INVENTION

One of the objectives of the invention is to provide novel particles loaded with at least one active principle (AP) and which release the AP over a prolonged period of time of several days, or even several weeks.

Another objective of the invention is to provide novel particles forming a stable suspension in aqueous solution.

Another objective of the invention is to provide novel particles loaded with AP, which are stable in the lyophilized form.

Another objective of the invention is to provide novel particles capable of being stored in the lyophilized form.

Another objective of the invention is to provide novel particles which can be easily redispersed after lyophilization.

Another objective of the invention is to provide novel particles which release a protein that has retained its biological activity.

Another objective of the invention is to provide a novel process for the preparation of these microparticles.

Another objective of the invention is to provide a solid pharmaceutical formulation for the sustained release AP, in particular a dry powder form for inhalation and pulmonary administration.

After lengthy and extensive research, the Applicant has unexpectedly found that mixing, under specific conditions, two polyelectrolyte polymers (e.g., copolyamino acid polymers) of opposite polarity, wherein at lest one the polymers carries hydrophobic groups that are associated with at least one AP, results in the formation of particles with a size of between 1 and 100 microns capable of the AP (for example a protein or a peptide) in vitro or in vivo over a prolonged period of time.

Accordingly, the present invention first relates to particles for the sustained release of at least one active principle (AP), wherein said particles comprise:
  a) a first polyelectrolyte polymer (PE1), preferably a linear α-polyamino acid, in a charged state, carrying side hydrophobic groups (GH), said first polyelectrolyte polymer (PE1) spontaneously forming, in water, a colloidal solution of particles at at least one pHm value of the pH between 3 and 8;
  b) a second polyelectrolyte polymer (PE2), preferably a linear α-polyamino acid, of opposite polarity to the first polyelectrolyte polymer (PE1), said second polyelectrolyte polymer (PE2) forming, in water, a solution or a colloidal solution at said pHm value of the pH; provided that, if the first electrolyte polymer (PE1) is a polyamino acid, then the second polyelectrolyte polymer (PE2) is neither polylysine nor polyethyleneimine; and
  c) at least one active principle (AP) associated noncovalently with the particles of the colloidal solution of the first polyelectrolyte polymer (PE1);
wherein said particles for the sustained release of at least one active principle (AP) are obtained by mixing, at a pH equal to pHm, the first polyelectrolyte polymer (PE1), in the form of a colloidal solution of particles associated with the active principle (AP), with the second polyelectrolyte polymer (PE2), in the form of a solution or colloidal solution.

The invention also relates to a process for the preparation of particles for the sustained release of at least one active principle (AP), these particles being in particular those described above, wherein said process comprises the following steps:
  1) preparing, at a pHm value of the pH between 3 and 8, an aqueous colloidal solution of a first polyelectrolyte polymer (PE1) in a charged state, carrying side hydrophobic groups (GH), wherein said first polyelectrolyte polymer (PE1) can spontaneously form, in water, a colloidal solution of particles at the pHm value of the pH;
  2) adding at least one active principle (AP) to the first polyelectrolyte polymer (PE1) obtained in step 1, wherein said active principle associate noncovalently with the particles of the colloidal solution of said first polyelectrolyte polymer (PE1);
  3) preparing a second polyelectrolyte polymer (PE2) of opposite polarity to the first polyelectrolyte polymer (PE1), wherein said second polyelectrolyte polymer (PE2) can form, in water, a solution or a colloidal solution at the pHm value of the pH; and
  4) mixing, at a pH equal to pHm, the first polyelectrolyte polymer (PE1), in the form of a colloidal solution of particles associated with the active principle (AP) obtained in step 2), with the second polyelectrolyte polymer (PE2), in the form of a solution or colloidal solution obtained in step 3), with the proviso that, if the first electrolyte polymer (PE1) is a polyamino acid, then the second polyelectrolyte polymer (PE2) is neither polylysine nor polyethyleneimine;

The invention also relates to particles for the sustained release of at least one active principle (AP), wherein said particles comprise:
  a) a first polyelectrolyte polymer (PE1), preferably a linear α-polyamino acid, in a charged state, carrying side hydrophobic groups (GH), said first polyelectrolyte polymer (PE1) spontaneously forming, in water, a colloidal solution of particles at at least one pHm value of the pH of between 3 and 8;
  b) a second polyelectrolyte polymer (PE2), preferably a linear α-polyamino acid, of opposite polarity to the first polyelectrolyte polymer (PE1), carrying side hydrophobic groups (GH), said second polyelectrolyte polymer (PE2) forming, in water, a solution or a colloidal solution at said pHm value of the pH; and
  c) at least one active principle (AP) associated noncovalently with the particles of the colloidal solution of the first polyelectrolyte polymer (PE1);
wherein said particles for the sustained release of at least one active principle (AP) are obtained by mixing, at a pH equal to pHm, the first polyelectrolyte polymer (PE1), in the form of a colloidal solution of particles associated with the active principle (AP), with the second polyelectrolyte polymer (PE2) in the form of a solution or colloidal solution.

The invention also relates to a process for the preparation of particles for the sustained release of at least one active principle (AP), said particles being in particular those described above, wherein said process comprises the following steps:
  1) preparing, at a pHm value of the pH between 3 and 8, an aqueous colloidal solution of a first polyelectrolyte polymer (PE1) in a charged state, carrying side hydrophobic groups (GH), wherein first polyelectrolyte polymer (PE1) can spontaneously forming, in water, a colloidal solution of particles at the pHm value of the pH;
  2) adding at least one active principle (AP) to the first polyelectrolyte polymer (PE1) obtained in step 1, wherein said active principle associate noncovalently with the particles of the colloidal solution of said first polyelectrolyte polymer (PE1);
  3) preparing a second polyelectrolyte polymer (PE2) of opposite polarity to the first polyelectrolyte polymer (PE1), carrying side hydrophobic groups (GH), wherein said second polyelectrolyte polymer (PE2) forms, in water, a solution or a colloidal solution at said pHm value of the pH; and
  4) mixing, at a pH equal to pHm, the first polyelectrolyte polymer (PE1), in a form of a colloidal solution of particles with which the active principle (AP) is associated obtained in step 2), with the second polyelectrolyte polymer (PE2), in the form of a solution or colloidal solution obtained in step 3).

The invention also relates to a pharmaceutical formulation for the sustained release of at least one active principle (AP), said formulation comprising particles as described above.

The invention also relates to a process for the preparation of medicaments, in particular for parenteral, mucosal, subcutaneous, intramuscular, intradermal, intraperitoneal or intracerebral administration or administration into a tumor, indeed even administration by the oral, nasal, pulmonary, vaginal, transdermal or ocular route, consisting essentially in employing at least one formulation as defined above.

DETAILED DESCRIPTION OF THE INVENTION

Definitions

In the present description, the term "solution" is understood to mean a homogeneous mixture of solvent and polymer in the form of individual chains.

In the present description, the term "colloidal solution" is understood to mean a suspension of particles, the mean diameter of which, measured by the T' test, is less than or equal to 0.5 μm.

In the present description, the term "half-neutralization pH" is understood to mean the pH at which half of the ionizable groups of a compound are ionized.

In the present description, the term "pHm" is understood to mean the pH at which the reaction of mixing the first polyelectrolyte polymer (PE1), with which the active principle (AP) is associated, with the second polyelectrolyte polymer (PE2) is carried out.

In the present description, the physiological pH is defined as being, for example, equal to 7.2±0.4.

In the present description, the term "polyelectrolyte" is understood to mean a polymer carrying groups capable of ionizing in water, thereby creating charges on the polymer.

In the present description, the term "polyampholyte" is understood to mean a polyelectrolyte carrying at least two types of groups which respectively dissociate to give anionic and cationic groups.

In the present description, the expression "to carry" means that the group carried is pendant (or hanging), that is to say that said group is a side group with respect to the main chain of the polymer. In particular, when the polymer is a polyamino acid comprising "amino acid" residues, a pendant group is a side group with respect to the "amino acid" residues and is a substitute of the carbonyl functional group in the γ position of the "amino acid" residue which carries it.

In the present description, the term "polarity of a polyelectrolyte" is understood to mean the polarity of the overall charge carried by this polyelectrolyte at the pHm value of the pH.

In the present description, the term "bulk density" is understood to mean the volume occupied by 1 g of particles. The bulk density is measured by any method known to a person skilled in the art, such as the density gradient method.

In the present description, the term "small molecule" is understood to mean molecule whose molecular weight is less than 1 kDa.

The T test may be used to measure the size of the particles according to the invention resulting from the association between the first polyelectrolyte polymer (PE1) and second polyelectrolyte polymer (PE2). The T' test is preferably used to evaluate the size of the particles of the colloidal solution of the first polyelectrolyte polymer (PE1).

The result of the T test is a median diameter D50 such that 50% of the particles present in the sample have a size of less than or equal to this value (D50).

The result of the T' test is a mean hydrodynamic diameter.
T Test for Measuring the Size of the Microparticles by Laser Diffraction:

This test provides D50, which, as mentioned above, is defined as the median diameter value such that 50% of the objects analyzed have a size smaller or equal to D50. This diameter of the particles according to the invention is measured according to the procedure defined below:

The solutions of particles are prepared by diluting 400 μl of the sample to be analyzed with 600 μl of demineralized water in a 5 ml test tube and by then vortexing the preparation for 10 seconds (10±5). These solutions are subsequently introduced dropwise into the measurement cell until the obscuration is between 5% and 20% and then they are analyzed by light diffraction using a device of Malvern Mastersizer 2000 type operating with two wavelengths 466 and 632 nm. The D50 of the particles is calculated from the Mie theory using the following refractive indices:

$n_{fluid}=1.33+i.0$, $n_{polymer}=1.59+i.0$, and the Fraunhofer approximations, as described in standard ISO 13320.
T' Test for Measuring the Size of the Nanoparticles by Quasielastic Light Scattering:

The mean hydrodynamic diameter of the particles of polymer according to the invention is measured using the following Md procedure:

The polymer solutions are prepared at concentrations of 1 or 2 mg/ml in 0.15M NaCl medium and are stirred for 24 h. These solutions are subsequently filtered through a 0.8-0.2 μg/m filter before analyzing them in dynamic light scattering using a device of Malvern Compact Goniometer System type operating with a vertically polarized He—Ne laser beam with a wavelength of 632.8 nm. The hydrodynamic diameter of the polymer nanoparticles is calculated from the autocorrelation function of the electric field by the method of cumulants, as described in "Surfactant Science Series", volume 22, Surfactant Solutions, edited by R. Zana, Chap. 3, M. Dekker, 1984.
L Test for Measuring the Release of the Active Principle:

50 μl of formulation are injected into a cube with a side length of 1.5 cm, of polyurethane/polyether (PU-PE) foam bathed by a flow of 2.83 ml/h of an aqueous medium comprising 30 mg/g of bovine albumin fraction V (Aldrich), 0.01 M of phosphate buffer, 0.0027 M of potassium chloride, 0.137 M of sodium chloride (PBS from Aldrich) and 0.015 M of ammonium acetate (Aldrich). Samples are regularly withdrawn from the continuous phase, the protein content of which is analyzed by ELISA (Immunotech IM3193 kit).

It is then possible to plot the total weight of protein released by adding the values determined for each of the samples withdrawn and to relate it to the total amount injected.

Within the meaning of the invention, the term "protein" denotes interchangeably a protein and a peptide, whether an oligopeptide or a polypeptide. This protein or this peptide may or may not be modified, for example, by grafting of one or more polyoxyethylene groups.

The first and second polyelectrolyte polymers (PE1) and (PE2) are biocompatible and biodegradable linear polymers carrying ionizable anionic and/or cationic groups, for example amine or carboxylic acid functional groups. Preferably, the polymer (PE1) or (PE2) carries ionizable groups of a given polarity (anionic or cationic).

Such polymers are, for example, polyamino acids, anionic polysaccharides, such as dextran sulfate, carboxymethylcellulose, gum arabic, hyaluronic acid and its derivatives, polygalacturonics or polyglucuronics, or cationic polysaccharides, such as chitosan, or also collagen and its derivatives of gelatin type.

The possibility is not excluded for a polymer carrying ionizable groups of a given polarity to also carry a small fraction, e.g., from 1 to 30 molar %, of ionizable groups of the opposite polarity. In addition to the ionizable anionic and/or cationic groups and hydrophobic groups, the first or second polyelectrolyte polymer (PE1) or (PE2) can optionally also carry nonionizable groups, such as groups chosen from a hydroxyethylamino-radical, from an alkylene glycol or from a polyalkylene glycol.

The net charge of the polymer depends on the value of the pH with respect to the half-neutralization pH of the polymer. Thus, for a polyelectrolyte carrying anionic carboxylic groups, the net charge of the polymer will be in the region of zero at a pH two units below the half-neutralization pH. Virtually all the anionic functional groups will be ionized two pH units above the half-neutralization pH. On the other hand, for a polymer carrying cationic functional groups, the net charge is reduced to zero when the pH exceeds the half-neutralization pH by approximately two units.

In the present invention, the number of charges carried by the first or second polyelectrolyte polymer (PE1, PE2) under the mixing conditions at the pHm value of the pH, is obtained by a conventional acid/base titration method:

A concentrated 2 mg/ml polyelectrolyte solution comprising 0.15 M of sodium chloride is brought to pH 3 by addition of 1 M acetic acid or 1 M sodium hydroxide solution. This solution is subsequently titrated with a 0.05 M sodium hydroxide solution, the change in the pH being recorded as a function of the volume of sodium hydroxide added. The detection of the equivalence point (volume and pH), for example using the double tangent method, allows to detect the pH for which all the ionizable groups are ionized, i.e., wherein the degree of ionization is equal to 1. It is then possible, starting from this point, to obtain the degree of ionization of the polyelectrolyte for any value of the pH. The half-neutralization pH, i.e., the pH for which the degree of ionization is equal to 0.5, can thus be obtained. It is also possible to determine the degree of ionization of the polyelectrolyte for the pHm value of the pH. In the specific case where the equivalence point is outside the pH range of between 3 and 9, all the ionizable groups are considered as ionized over this pH range, that is to say that the degree of ionization is equal to 1 for pH values of between 3 and 9.

Advantageously, the first and second polyelectrolyte polymers (PE1, PE2) can be linear poly(α-amino acid)s (with the proviso that if PE1 is a linear polyamino acid, PE2 is neither polylysine, nor polyethyleneimine).

Within the meaning of the invention and throughout the present document, the term "polyamino acid" encompasses both natural polyamino acids and synthetic polyamino acids, including oligoamino acids comprising from 2 to 20 "amino acid" residues and polyamino acids comprising more than 20 "amino acids" residues.

Preferably, the polyamino acids used in the present invention are oligomers or homopolymers comprising glutamic or aspartic acid repeat units or copolymers comprising a mixture of these two types of "amino acid" residues. The residues under consideration in these polymers are amino acids having the D or L or D/L configuration and are bonded via their α or γ positions for the glutamate or glutamic residues and their α or β positions for the aspartic or aspartate residue.

The preferred "amino acid" residues of the main polyamino acid chain are those having the L configuration and a bond of α type.

According to an even more preferred embodiment of the invention, the first and second polyelectrolyte polymers (PE1, PE2) can be polyamino acids, or pharmaceutically acceptable salts thereof, wherein the main chain is formed by residues chosen from the group consisting of aspartic residues, glutamic residues and their combinations, at least a portion of these units being modified by grafting of at least one hydrophobic group (GH) for at least the first polyelectrolyte polymer (PE1).

Polymer PE2 may also carry hydrophobic groups.

According to a first embodiment, these polyamino acids are as described in PCT patent application WO-A-00/30618, wherein the hydrophobic groups (GH) are identical or different from one another, and are selected from the group consisting of:
(i) linear or branched, preferably linear $C_1$-$C_{20}$ and more preferably still $C_2$-$C_{18}$, alkyls, acyls or alkenyls;
(ii) hydrocarbon groups comprising one or more heteroatoms, preferably hydrocarbon groups comprising oxygen and/or sulfur and more preferably still hydrocarbon groups with the following formula:

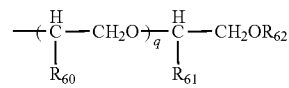

in which:
$R_{60}$ is a linear or branched, preferably linear $C_1$-$C_{20}$ and more preferably still $C_2$-$C_{18}$, alkyl, acyl or alkenyl radical,
$R_{61}$ and $R_{62}$ are identical or different from one another and correspond to hydrogen or to a linear or branched, preferably linear $C_1$-$C_{20}$ and more preferably still $C_2$-$C_{18}$, alkyl, acyl or alkenyl radical,
q=1 to 100;
(iii) aryls, aralkyls or alkylaryls, preferably aryls; and
(iv) hydrophobic derivatives, preferably the phosphatidylethanolamino- group, or groups chosen from: octyloxy-, dodecyloxy-, tetradecyloxy-, hexadecyloxy-, octadecyloxy-, 9-octadecenyloxy-, tocophéryloxy- or cholesteryloxy- groups.

The term "hydrocarbon groups" is understood to mean, within the meaning of the present invention, groups comprising in particular hydrogen and carbon atoms.

Preferably, in this embodiment, the hydrophobic groups are selected from the group consisting of: methyl, ethyl, propyl, dodecyl, hexadecyl and octadecyl.

Particularly preferably, the hydrophobic groups (GH) are chosen from the group consisting of:
linear or branched $C_8$ to $C_{30}$ alkyls which can optionally comprise at least one unsaturation and/or at least one heteroatom,
$C_8$ to $C_{30}$ alkylaryls or arylalkyls which can optionally comprise at least one unsaturation and/or at least one heteroatom, and
$C_8$ to $C_{30}$ (poly)cyclic compounds which can optionally comprise at least one unsaturation and/or at least one heteroatom.

More specifically, at least one of the hydrophobic groups (GH) is obtained by grafting from a precursor chosen from the group consisting of: octanol, dodecanol, tetradecanol, hexadecanol, octadecanol, oleyl alcohol, tocopherol and cholesterol.

According to an embodiment of the invention, one of the polyelectrolyte polymers (PE1, PE2), or pharmaceutically acceptable salt thereof, has the following formula (I):

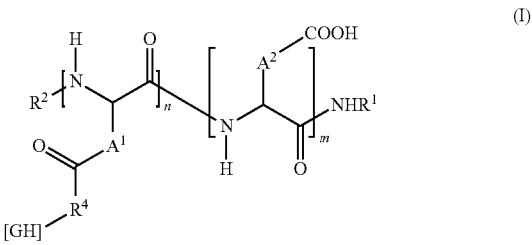

in which:
$R^1$ is H, a linear $C_2$ to $C_{10}$ or branched $C_3$ to $C_{10}$ alkyl, benzyl, —$R^4$-[GH], or $R^1$ forms, with NH, a terminal amino acid residue;
$R^2$ is H, a linear $C_2$ to $C_{10}$ or branched $C_3$ to $C_{10}$ acyl group, a pyroglutamate or —$R^4$-[GH];
$R^4$ is a direct bond or a "spacer" based on 1 to 4 amino acid residues;

$A^1$ and $A^2$ independently are —CH$_2$— (aspartic residue) or —CH$_2$—CH$_2$— (glutamic residue);

n/(n+m) is defined as the molar degree of grafting and its value is sufficiently low for the polymer dissolved in water at pH 7 and at 25° C. to form a colloidal suspension of polymer particles;

n+m varies from 10 to 1000, preferably between 50 and 300;

GH represents a hydrophobic group comprising 6 to 30 carbon atoms or is chosen from groups defined in the above paragraphs (i), (ii), (iii) and (iv).

For further details regarding the preparation and synthesis of polyamino acids of formula (I), see patent applications FR 02 07008 and FR 03 50190.

According to another possibility, the polyelectrolyte polymer PE2, or a pharmaceutically acceptable salt thereof, has one of the following formulae (II), (III) and (IV):

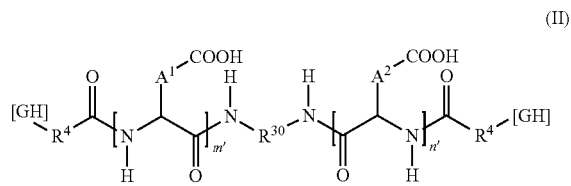
(II)

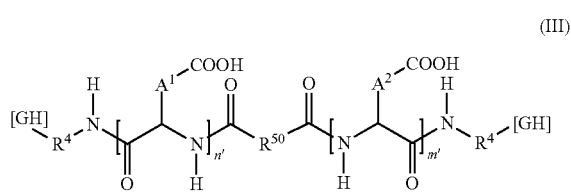
(III)

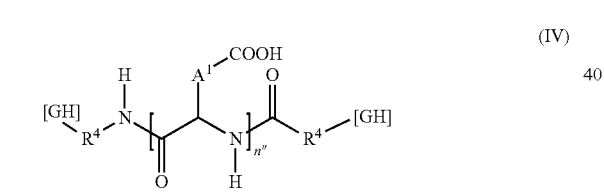
(IV)

in which:

GH represents a hydrophobic group comprising 6 to 30 carbon atoms;

$R^{30}$ is a linear $C_2$ to $C_6$ alkyl group;

$R^{50}$ is a $C_2$ to $C_6$ diamino, dialkoxy or alkyl group;

$R^4$ represents a direct bond or a "spacer" based on 1 to 4 amino acid residues;

$A^1$ and $A^2$ independently are —CH$_2$— (aspartic residue) or —CH$_2$—CH$_2$— (glutamic residue);

n'+m' or n" is defined as the degree of polymerization and varies from 10 to 1000, preferably between 50 and 300.

For further details regarding the preparation and synthesis of polyamino acids of formula (II), (III) and (IV), see patent application FR 03 50641.

According to another possibility, one of the polyelectrolyte polymers (PE1, PE2), or a pharmaceutically acceptable salt thereof, has the following formula (V):

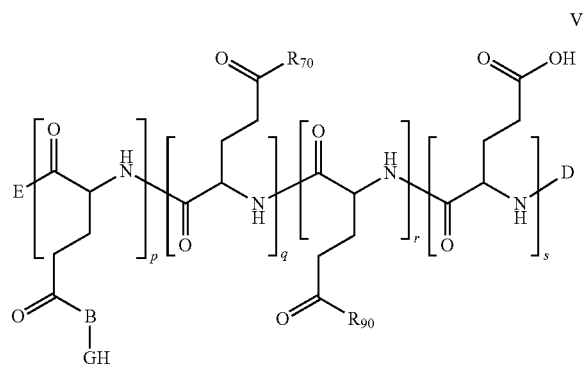
(V)

in which:

E is:
  an —NHR group in which R is H, a linear $C_2$ to $C_{10}$ or branched $C_3$ to $C_{10}$ alkyl or a benzyl,
  a terminal amino acid residue or a terminal amino acid derivative with the following formula:

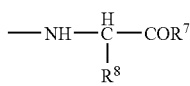

in which:

$R^7$ is OH, OR$^9$ or NHR$^{10}$ and $R^8$, $R^9$ and $R^{10}$ independently are H, a linear $C_2$ to $C_{10}$ or branched $C_3$ to $C_{10}$ alkyl or a benzyl;

B is a direct bond or a divalent, trivalent or tetravalent bonding group preferably selected from the following groups:

—O—, —NH—, —N($C_1$ to $C_5$alkyl)-, a residue of amino acid (preferably of a natural amino acid), of diol, of triol, of diamine, of triamine, of aminoalcohol or of hydroxy acid comprising from 1 to 6 carbon atoms;

D is H, a linear $C_2$ to $C_{10}$ or branched $C_3$ to $C_{10}$ acyl group or a pyroglutamate;

GH represents a hydrophobic group comprising 6 to 30 carbon atoms;

$R_{70}$ is a group selected from the group consisting of:
  —NH—(CH$_2$)$_w$—NH$_3^+$ in which w is between 2 and 6, and preferably w is 4,
  —NH—(CH$_2$)$_4$—NH—C(=NH)—NH$_3^+$,
  —O—(CH$_2$)$_2$—NH$_3^+$,
  —O—(CH$_2$)$_2$—N$^+$(CH$_3$)$_3$,

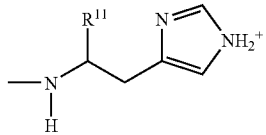

wherein —R$^{11}$ is —H, —CO$_2$H, an alkyl ester (preferably —COOMe and —COOEt), —CH$_2$OH, —C(=O)—NH$_2$, —C(=O)—NH—CH$_3$ or —C(=O)—N(CH$_3$)$_2$; and an amino acid residue or an amino acid derivative of the following formula:

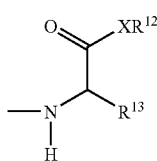

in which:
X is an oxygen or —NH—,
—$R^{12}$ is H, a linear $C_2$ to $C_{10}$ or branched $C_3$ to $C_{10}$ alkyl or a benzyl,
—$R^{13}$ is —$(CH_2)_4NH_3^+$, —$(CH_2)_3$—NH—C(=NH)—$NH_3^+$, —$(CH_2)_3NH_3^+$;

wherein the counteranion of $R_{70}$ is a chloride, a sulfate, a phosphate or an acetate, preferably a chloride;

$R_{90}$ is a hydroxyethylamino-, an allylene glycol residue or a polyoxyalkylene residue;

p, q, r and s are positive integers;

(p)/(p+q+r+s) is defined as the molar degree of grafting of the hydrophobic groups GH and varies from 2 to 99 molar % and preferably between 5 and 50 molar %, provided that each copolymer chain has, on average, at least 3 hydrophobic grafts;

(q)/(p+q+r+s) is defined as the molar degree of grafting of the cationic groups and varies from 1 to 99 molar %;

(p+q+r+s) varies from 10 to 1000, preferably between 30 and 500;

(r)/(p+q+r+s) varies from 0 to 98 molar %; and (s)/(p+q+r+s) varies from 0 to 98 molar %.

The lysine, ornithine and arginine derivatives can, for example, be ethyl and methyl esters, amides and methylated amides.

Preferably, according to this alternative form, the hydrophobic groups GH and the cationic groups are positioned randomly as pendant groups.

Furthermore, it is preferable for the molar degree of grafting of the polyglutamates with hydrophobic units to be between 2 and 99% and preferably between 5 and 50%, provided that each polymer chain has, on average, at least 3 hydrophobic grafts.

The ratio (q)/(p+q+r+s) of the polyglutamates means that they can comprise from 1 to approximately 97 molar % of groups comprising a cationic charge.

The ratio (s)/(p+q+r+s) of the polyglutamates means that they can be anionic, neutral or cationic at neutral pH.

For further details regarding the preparation and synthesis of polyamino acids of formula (V) derived from histidine, see patent application FR 05 53302.

For further details regarding the preparation and synthesis of polyamino acids of formula (V) other than those derived from histidine, see French patent application FR 07 03185.

According to an advantageous embodiment, $R^4$ or B represents, in the preceding formulae, a direct bond.

According to another embodiment, one of the polyelectrolyte polymers (PE1, PE2) comprises hydroxyalkyl(preferably ethyl)glutamine residues and a multiplicity of pendant hydrophobic groups (GH) which are identical or different from one another. The hydroxyalkylglutamine units can also carry hydroxyalkylamine groups. These hydroxyalkylamine groups are, preferably, linked to the copolymer via an amide bond. Hydroxyalkylamine groups which can be used to functionalize the glutamate residues of these hydroxyalkylglutamine residues may be identical or different from one another and are, for example, selected from the following groups: 2-hydroxyethylamino, 3-hydroxypropylamino, 2,3-dihydroxypropylamino, tris(hydroxymethyl)methylamino and 6-hydroxyhexylamino.

Advantageously, at least one of the hydrophobic groups GH used in the present invention is included in a hydrophobic graft comprising at least one spacing joint (or unit) (spacer) allowing binding of the hydrophobic group (GH) to a copolyglutamate chain (for example, a copolyglutamate backbone main chain). This joint can comprise, e.g., at least one direct covalent bond and/or at least one amide bond and/or at least one ester bond. For example, the joint can belong to the group consisting of: "amino acid" residues other than the constituent monomeric units of the copolyglutamate, aminoalcohol derivatives, polyamine (for example diamine) derivative, polyol (for example diol) derivatives and hydroxy acid derivatives. The grafting of GHs to the copolyglutamate or polyalkylglutamine chain can involve the use of GH precursors that can be linked to the copolyglutamate chain or to hydroxyalkylglutamine residues. Precursors of the GHs are in practice, and without limitation, selected from the group consisting of alcohols and amines, which are easily functionalized by a person skilled in the art. For further details regarding these hydroxyalkyl(preferably ethyl)glutamine residues, see FR-A-2 881 140.

According to an advantageous embodiment, in particular according to at least one of the various possibilities described above, all or a portion of the hydrophobic groups (GH) used in the present invention are selected independently from the group consisting of:

a linear or branched alkoxy which comprises from 6 to 30 carbon atoms and which can comprise at least one heteroatom (preferably O and/or N and/or S) and/or at least one unsaturation, an alkoxy which comprises from 6 to 30 carbon atoms and which has one or more annulated carbocycles and which optionally comprises at least one unsaturation and/or at least one heteroatom (preferably O and/or N and/or S); and an alkoxyaryl or an aryloxyalkyl of 7 to 30 carbon atoms and which can comprise at least one unsaturation and/or at least one heteroatom (preferably O and/or N and/or S).

According to another advantageous embodiment, in particular according to at least one of the various possibilities described above, the hydrophobic group (GH) results from an alcoholic precursor selected from the group consisting of: octanol, dodecanol, tetradecanol, hexadecanol, octadecanol, oleyl alcohol, tocopherol and cholesterol, and $R^4$ is a direct bond.

According to another advantageous embodiment, the hydrophobic groups (GH), in particular according to at least one of the various possibilities described above, each represents, independently of one another, a monovalent group of the following formula:

[GH]

in which:
$R^5$ is methyl (alanine), isopropyl (valine), isobutyl (leucine), sec-butyl (isoleucine) or benzyl (phenylalanine);

$R^6$ is a hydrophobic group comprising from 6 to 30 carbon atoms; and l varies from 0 to 6.

According to a noteworthy characteristic of the invention, all or a portion of the hydrophobic groups $R^6$ of the hydrophobic groups (GH) are selected independently from the group of consisting of:

- a linear or branched alkoxy which comprises from 6 to 30 carbon atoms and which can comprise at least one heteroatom (preferably O and/or N and/or S) and/or at least one unsaturation,
- an alkoxy which comprises from 6 to 30 carbon atoms and which has one or more annulated carbocycles and which optionally comprises at least one unsaturation and/or at least one heteroatom (preferably O and/or N and/or S); and
- an alkoxyaryl or an aryloxyalkyl of 7 to 30 carbon atoms and which can comprise at least one unsaturation and/or at least one heteroatom (preferably O and/or N and/or S).

In practice, and without limitation, said hydrophobic group $R^6$ results from an alcoholic precursor selected from the group consisting of: octanol, dodecanol, tetradecanol, hexadecanol, octadecanol, oleyl alcohol, tocopherol and cholesterol.

Advantageously, the main chain of the polyelectrolyte polyamino acids (PE1, PE2) used in the invention is selected from the group consisting of α-L-glutamate homopolymers, α-L-glutamic homopolymers, α-L-aspartate homopolymers, α-L-aspartic homopolymers, α-L-aspartate/α-L-glutamate copolymers and α-L-aspartic/α-L-glutamic copolymers.

In a noteworthy way, the distribution of the aspartic and/or glutamic residues of the main polyamino acid chain of the polyelectrolyte polymer PE1 or PE2 is such that the polymer thus formed is either random or of a block or multiblock type.

According to a different method of characterization, a polyelectrolyte polymer PE1 or PE2 of the present invention has a molar mass which lies between 2 000 and 100 000 g/mol and preferably between 5 000 and 40 000 g/mol.

The degree of polymerization of the first and second polyelectrolyte polymers (PE, PE2) is between 50 and 500, preferably between 70 and 300.

The molar fraction of the polymer units in the main chain that are substituted by hydrophobic groups is between 1 and 40 molar %, preferably between 3 and 30 molar %.

The polymers used in the present invention are chosen from the various families described above so that they are cationic or anionic overall at the pH value equal to pHm.

An essential characteristic of the first polyelectrolyte polymer (PE1) carrying side hydrophobic groups is that it can spontaneously form a colloidal solution in water.

Without wishing to be bound by the theory, it may be hypothesized that the supramolecular association of the hydrophobic groups to form hydrophobic domains results in the formation of nanoparticles. Each nanoparticle is comprised of one or more chains of PE1 polymers more or less condensed around its hydrophobic domains. It should be understood that the polymers used in the invention comprise ionizable functional groups which are, according to the pH and the composition, either neutral (for example —COOH, —NH$_2$) or ionized (for example —COO$^-$, —NH$_3^+$). For this reason, the solubility in an aqueous phase directly depends on the level of ionized functional groups and thus on the pH. In aqueous solution, in the case of carboxyl groups, the counterion can be a metal cation, such as sodium, calcium or magnesium, or an organic cation, such as triethanolamine, tris(hydroxymethyl)aminomethane or a polyamine, such as polyethyleneimine. The counteranion of the cationic groups is preferably chosen from the group consisting of a chloride, a sulfate, a phosphate and an acetate.

Knowing the half-neutralization pH, a person skilled in the art is able to adjust the pH in order for the degree of ionization of the polymer to be sufficiently high and ensure the stability of the colloidal solution.

Polyelectrolytes of a polyamino acid type suitable for use in the present invention can be obtained, for example, by methods known in the art. Random polyamino acids can be obtained by grafting the hydrophobic graft, functionalized beforehand by "the spacer", directly to the polymer by a conventional coupling reaction. Block or multiblock polyamino acid polyelectrolytes can be obtained by sequential polymerization of the corresponding N-carboxyamino acid anhydrides (NCA).

A polyamino acid, homopolyglutamate, homopolyaspartate or a block, multiblock or random glutamate/aspartate copolymer, may be prepared, for example, according to conventional methods.

The most widely used technique for obtaining polyamino acid of α type is based on the polymerization of N-carboxyamino acid anhydrides (NCA), described, for example, in the article "*Biopolymers,* 1976, 15, 1869" and in the work by H. R. Kricheldorf, "*alpha-Amino acid N-carboxy Anhydrides and related Heterocycles*", Springer Verlag (1987). The NCA derivatives are preferably NCA-O-Me, NCA-O-Et or NCA-O-Bz derivatives (Me=Methyl, Et=Ethyl and Bz=Benzyl). The polymers are subsequently hydrolyzed under conditions appropriate for obtaining the polymer in its acid form. These methods are inspired by the description given in patent FR-A-2 801 226 granted to the Applicant. A certain number of polymers which can be used according to the invention, for example, poly(α-L-aspartic), poly(α-L-glutamic), poly(α-D-glutamic) and poly(γ-L-glutamic) with variable weights, are available commercially. Polyaspartic of the α,β type can be obtained by condensation of aspartic acid (to obtain a polysuccinimide), followed by basic hydrolysis (cf. Tomida et al., *Polymer,* 1997, 38, 4733-36).

The coupling of a hydrophobic graft GH to an acid functional group of the polymer is easily carried out by reaction of the polyamino acid in the presence of a carbodiimide as coupling agent and optionally a catalyst, such as 4-dimethylaminopyridine, and in an appropriate solvent, such as dimethylformamide (DMF), N-methylpyrrolidone (NMP) or dimethyl sulfoxide (DMSO). The carbodiimide is, for example, dicyclohexylcarbodiimide or diisopropylcarbodiimide. The degree of grafting is chemically controlled by the stoichiometry of the constituents and reactants or the reaction time. The hydrophobic grafts functionalized by a "spacer" are obtained by conventional peptide coupling or by direct condensation by acid catalysis.

The coupling of cationic and optionally neutral groups to an acid functional group of the polymer is carried out simultaneously in a second stage in the presence of a chloroformate as coupling agent and in an appropriate solvent, such as dimethylformamide, N-methylpyrrolidone (NMP) or dimethyl sulfoxide (DMSO).

In cases where the cationic group comprises two amine functional groups which are not chemically differentiated (e.g. linear diamine), it can be introduced in a form in which one of the two functional groups is protected. A final stage of cleavage of the protective group is then added.

The polymerization chemistry and the reactions for coupling the groups are conventional and well known to one skilled in the art (see, for example, the patents or patent applications of the Applicant mentioned above).

NCA derivatives synthesized beforehand with the hydrophobic graft are used for the synthesis of block or multiblock copolymer. For example, the NCA-hydrophobe derivative is copolymerized with the NCA-O-benzyl and then the benzyl groups are selectively removed by hydrolysis.

Examples of particularly preferred associations of polyelectrolyte polymers (PE1 and PE2) according to the invention are described in the examples below.

An essential characteristic of the polymers used in the invention is that the first polyelectrolyte polymer (PE1) is in the form of a colloidal solution and that the second polyelectrolyte polymer (PE2) is in the form of a solution or colloidal solution for at least one value, pHm, of the pH between 3 and 8.

In order to fulfill this condition, the half-neutralization pH of the cationic polymer will be sufficiently high, for example greater than 5.5, preferably greater than 6 or even greater than 8; and the half-neutralization pH of the anionic polymer will be sufficiently low, for example less than 6.5, preferably less than 6.0 or even less than 5.5.

More particularly, in an alternative form according to which the first polyelectrolyte polymer (PE1) is anionic, the latter is chosen so that it exhibits a half-neutralization pH of between 3 and 6.5 and preferably between 4.5 and 6.5. According to this alternative form, the first polyelectrolyte polymer (PE1) forms a colloidal solution for a pHm value of the pH of between 6 and 8.

Such a polymer PE1 is described in particular in example 1a).

In this case, and according to a first possibility, the second electrolyte polymer (PE2) is cationic and forms a colloidal solution at a pH of less than 8. Preferably, the second polyelectrolyte polymer (PE2) is chosen so that it exhibits a half-neutralization pH of greater than 8. Such a polymer PE2 is described in particular in example 1d).

Thus, according to this first possibility, the first polyelectrolyte polymer (PE1) forms a colloidal solution and the second polyelectrolyte polymer (PE2) forms a solution or a colloidal solution for the pHm value of the pH of between 6 and 8.

In this case, according to an important characteristic of the invention, the ratio of the weight of the first polyelectrolyte polymer (PE1) to the weight of the second polyelectrolyte polymer (PE2) is chosen in order for the charge ratio Z, the ratio of the number of moles of cationic ionized groups to the number of moles of anionic ionized groups, measured at pHm, to be between 0.25 and 3 and preferably between 0.25 and 1.5.

According to a second possibility, the second polyelectrolyte polymer (PE2) is cationic and forms a colloidal solution at a pH of less than 6 and a precipitate at a pH of greater than 6.5. Preferably, the second polyelectrolyte polymer (PE2) is chosen so that it exhibits a half-neutralization pH of between 5.5 and 7. Such a polymer PE2 is described in particular in example 1c). In this case, according to an important embodiment of the invention, the first polyelectrolyte polymer (PE1) forms a colloidal solution and the second polyelectrolyte polymer (PE2) forms a solution or a colloidal solution for a value of the pH, pHm, of between 3 and 6. The ratio of the weight of the first polyelectrolyte polymer (PE1) to the weight of the second electrolyte polymer (PE2) is chosen in order for the charge ratio Z, measured at pHm, to be between 3.5 and 30, preferably between 5 and 15 and more preferably still between 8 and 12.

In another alternative form according to which the first polyelectrolyte polymer (PE1) is cationic, the latter is chosen so that it exhibits a half-neutralization pH of greater than 5. In this case, the second polyelectrolyte polymer (PE2) is anionic and is chosen so that it exhibits a half-neutralization pH of between 3 and 6.5 and preferably between 4.5 and 6.5.

The particles according to the invention exhibit, at physiological pH, a size, measured in a T test, of between 1 and 100 microns.

Advantageously, the particles according to the invention are not chemically crosslinked.

In a specific implementation of the invention, the particles exhibit, at physiological pH, a high polymer bulk density of between 0.15 and 1.1, preferably of between 0.3 and 1.0 and more preferably still of between 0.5 and 1.0. A high polymer density reflects the existence within the particles of a dense network of polymer chains. Without wishing to be bound by the theory, it may be supposed that this dense network slows down the diffusion of the active principle (AP) present in the particles according to the invention to the external medium and thus contributes to slowing down its release. A surprising aspect of the dense particles according to the invention is that the network of polymer chains of which they are composed slows down the release of the active principle (AP) without, however, trapping this same active principle (AP) at the core of the particles. Thus, the transporter according to the invention allows both prolonged release of the active principle (AP) and good bioavailability.

In some cases, and in particular in cases of peptides or proteins with a strong affinity with the microparticles according to the invention, it can be advantageous to modulate the AP release speed, so as to accelerate the release, and/or to improve its bioavailability. After numerous tests, it has been demonstrated by the Applicant that the release of the protein or the peptide can be expedited when the PE1 or PE2 polymer, of a given polarity, also carries ionizable groups of the opposite polarity and/or non ionizable groups such as hydroxyethylamino-substituted groups.

Thus, in a specific implementation of the invention, one of the two polymers PE1 or PE2 simultaneously comprises:
 from 15 to 50 molar % of glutamate monomers;
 from 20 to 55 molar % of nonionizable monomers such as hydroxyethylamino-substituted groups;
 from 10 to 40 molar % of monomers carrying cationic groups which half-neutralization pH is greater than 8; and
 from 3 to 15 molar % of nonionizable monomers substituted by an hydrophobic group.

In another specific implementation of the invention, PE1 or PE2 polymer is cationic and simultaneously comprises:
 from 0 to 5 molar % glutamate monomers;
 from 50 to 85 molar % of nonionizable monomers such as hydroxyethylamino-substituted groups;
 from 10 to 40 molar % of monomers carrying cationic groups which half-neutralization pH is greater than 8; and
 from 3 to 15 molar % of nonionizable monomers substituted by an hydrophobic group.

In a specific implementation of the invention, the total concentration of polymer (PE1+PE2) present in the formulation is between 4 and 15 mg/ml, in particular when the active principle (AP) is a therapeutic protein. Within this concentration range, the formulation can be easily injected via a needle with a small diameter, for example a needle of gauge 27, indeed even 29 and even 31. Examples 3 and 4 describe such formulations in detail.

The active principle (AP) is preferably chosen from the group consisting of: proteins, glycoproteins, proteins bonded to one or more polyalkylene glycol chains [preferably polyethylene glycol (PEG): "PEGylated proteins"], peptides, polysaccharides, liposaccharides, oligonucleotides, polynucleotides and mixtures thereof, and, more preferably still, from the subgroup of erythropoietins, such as epoetin alfa, epoetin beta, darbepoetin, hemoglobin raffimer, their analogs or their derivatives; oxytocin, vasopressin, adrenocorticotropic hormone, epidermal growth factor, platelet-derived growth factor (PDGF), factors which stimulate hematopoiesis and mixtures thereof, blood factors, such as alteplase, tenecteplase, factor VII(a) or factor VII; hemoglobin, cytochromes, albumins, prolactin, luliberin, luteinizing hormone-releasing hormone (LHRH) and analogs, such as leuprolide, goserelin, triptorelin, buserelin or nafarelin; LHRH antagonists, LHRH competitors, human, porcine or bovine growth hormones (GHs), growth hormone-releasing factor, insulin, somatostatin, glucagon, interleukins or their mixtures (IL-2, IL-11, IL-12), interferons, such as interferon alfa, alfa-2b, beta, beta-1a or gamma; gastrin, tetragastrin, pentagastrin, urogastrone, secretin, calcitonin, enkephalin, endomorphins, angiotensins, thyrotropin-releasing hormone (TRH), tumor necrosis factor (TNF), nerve growth factor (NGF), growth factors, such as beclapermin, trafermin, ancestim or keratinocyte growth factor, granulocyte-colony stimulating factor (G-CSF), granulocyte-macrophage-colony stimulating factor (GM-CSF), macrophage-colony stimulating factor (M-CSF), heparinase, bone morphogenetic protein (BMP), hANP, glucagon-like peptide (GLP-1), VEG-F, recombinant hepatitis B surface antigen (rHBsAg), renin, cytokines, bradykinin, bacitracins, polymyxins, colistins, tyrocidine, gramicidins, etanercept, imiglucerase, drotrecogin alfa, cyclosporins and synthetic analogs, pharmaceutically active modifications and fragments of enzymes, of cytokines, of antibodies, of antigens and of vaccines, and antibodies, such as rituximab, infliximab, trastuzumab, adalimumab, omalizumab, tositumomab, efalizumab and cetuximab.

Other suitable active principles are polysaccharides (for example heparin) and oligo- or polynucleotides, DNA, RNA, iRNA, antibiotics and living cells. Another category of suitable active principles comprises pharmaceutical substances which act on the central nervous system, for example risperidone, zuclopenthixol, fluphenazine, perphenazine, flupentixol, haloperidol, fluspirilene, quetiapine, clozapine, amisulpride, sulpiride, ziprasidone, and the like.

According to an embodiment, the active principle is a hydrophobic, hydrophilic or amphiphilic small organic molecule belonging to the family of anthracyclines, taxoids or camptothecins or belonging to the family of peptides, such as leuprolide or cyclosporin, and mixtures thereof.

Within the meaning of the present account, a small molecule is in particular a small nonprotein molecule, for example devoid of amino acids.

According to another embodiment, the active principle is advantageously chosen from at least one of the following families of active substances: agents for the treatment of alcohol abuse, agents for the treatment of Alzheimer's disease, anesthetics, agents for the treatment of acromegaly, analgesics, antiasthmatics, agents for the treatment of allergies, anticancer agents, antiinflammatories, anticoagulants and antithrombotics, anticonvulsants, antiepileptics, antidiabetics, antiemetics, antiglaucomas, antihistaminics, antiinfectives, antibiotics, antifungals, antivirals, antiparkinsonians, anticholinergics, antitussives, carbonic anhydrase inhibitors, cardiovascular agents, hypolipidemics, antiarrythmics, vasodilators, antianginals, antihypertensives, vasoprotectants, cholinesterase inhibitors, agents for the treatment of disorders of the central nervous system, stimulants of the central nervous system, contraceptives, fertility promoters, inducers and inhibitors of uterine labor, agents for the treatment of mucoviscidosis, dopamine receptor agonists, agents for the treatment of endometriosis, agents for the treatment of erectile dysfunctions, agents for the treatment of fertility, agents for the treatment of gastrointestinal disorders, immunomodulators and immunosuppressants, agents for the treatment of memory disorders, antimigraines, muscle relaxants, nucleoside analogs, agents for the treatment of osteoporosis, parasympathomimetics, prostaglandins, psychotherapeutic agents, sedatives, hypnotics and tranquilizers, neuroleptics, anxiolytics, psychostimulants, antidepressants, agents for dermatological treatments, steroids and hormones, amphetamines, anorectics, nonanalgesic painkillers, barbiturates, benzodiazepines, laxatives, psychotropics and any combination of these products.

According to another aspects, the invention provides a process for the preparation of particles for the sustained release of at least one active principle, these particles being in particular those described above, wherein said process comprises the following steps:

1) preparing, at a pHm value of the pH between 3 and 8, an aqueous colloidal solution of a first polyelectrolyte polymer (PE1) in a charged state, carrying side hydrophobic groups (GH), wherein said first polyelectrolyte polymer (PE1) can spontaneously form, in water, a colloidal solution of particles at said pHm value of the pH;
2) adding at least one active principle (AP) to the first polyelectrolyte polymer (PE1) obtained in step 1, wherein said active principle associate noncovalently with the particles of the colloidal solution of said first polyelectrolyte polymer (PE1);
3) preparing a second polyelectrolyte polymer (PE2) of opposite polarity to the first polyelectrolyte polymer (PE1), wherein said second polyelectrolyte polymer (PE2) forms, in water, a solution or a colloidal solution at said pHm value of the pH; and
4) mixing, at a pH equal to pHm, the first polyelectrolyte polymer (PE1), in the form of a colloidal solution of particles with which the active principle (AP) is associated obtained in step 2), with the second polyelectrolyte polymer (PE2), in the form of a solution or colloidal solution obtained in step 3);

with the proviso that, if the first electrolyte polymer (PE1) is a polyamino acid, then the second polyelectrolyte polymer (PE2) is neither polylysine nor polyethyleneimine;

Another subject matter of the invention is a process for the preparation of particles for the sustained release of at least one active principle (AP), these particles corresponding in particular to some described above, wherein said process comprises the following steps:

1) preparing, at a pHm value of the pH between 3 and 8, an aqueous colloidal solution of a first polyelectrolyte polymer (PE1) in a charged state, carrying side hydrophobic groups (GH), wherein said first polyelectrolyte polymer (PE1) can spontaneously form, in water, a colloidal solution of particles at said pHm value of the pH;
2) adding at least one active principle (AP) to the first polyelectrolyte polymer (PE1) obtained in step 1, wherein said active principle associate noncovalently with the particles of the colloidal solution of said first polyelectrolyte polymer (PE1);
3) preparing a second polyelectrolyte polymer (PE2) of opposite polarity to the first polyelectrolyte polymer (PE1), carrying side hydrophobic groups (GH), wherein said second polyelectrolyte polymer (PE2) forms, in water, a solution or a colloidal solution at said pHm value of the pH;

4) mixing, at a pH equal to pHm, the first polyelectrolyte polymer (PE1), in the form of a colloidal solution of particles with which the active principle (AP) is associated obtained in step 2), with the second polyelectrolyte polymer (PE2), in the form of a solution or colloidal solution obtained in step 3).

An essential characteristic of the process according to the invention is that of spontaneously forming particles by simple mixing, at pHm, of a colloidal solution of particles of the first polyelectrolyte polymer (PE1) loaded with active principle (AP) and of a solution or of a colloidal solution of the second polyelectrolyte polymer (PE2) of opposite polarity.

The active principles, such as proteins, peptides or small molecules, can associate spontaneously with the first polymer (PE1) of polyamino acid type. The loading of the nanoparticles of the first polyelectrolyte polymer (PE1) with the active principle (AP) is carried out by simple mixing of a solution of active principle (AP) with a colloidal solution of the first polyelectrolyte polymer (PE1). This association is purely physical and does not involve the creation of a covalent bond between the active principle (AP) and the polymer (PE1). Without being bound by theory, it may be supposed that this nonspecific association takes place by hydrophobic and/or electrostatic interaction between the polymer (PE1) and the active principle (AP). It should be noted that it is not necessary, and often even undesirable, to bind the AP to the PE1 nanoparticles via specific receptors of peptide nature or of antigen/antibody or also enzyme/substrate type.

In a preferred embodiment of the process according to the invention, the reaction does not invention a step of chemical crosslinking of the particles obtained. The particles according to the invention are thus not chemically crosslinked but nevertheless release the active principle (AP) over a prolonged period of time. This absence of chemical crosslinking is a decisive advantage of the particles according to the invention. This is because the absence of chemical crosslinking prevents chemical decomposition of the active principle (AP) that is generally observed during reactions of crosslinking of the particles comprising the active principle (AP). This is because such a chemical crosslinking is generally carried out by activation of polymerizable entities and involves potentially denaturing agents, such as UV radiation or glutaraldehyde.

Advantageously, the process according to the invention comprises a step of dehydration of the suspension of particles which are obtained (for example by lyophilization or atomization) in order to obtain them in the form of a dry powder.

According to another aspects, a subject matter of the invention is a pharmaceutical formulation for the sustained release of at least one active principle (AP), which comprises an aqueous suspension of particles as are described above or those obtained by the process described above.

The present invention also relates to a solid pharmaceutical formulation for the prolonged release of at least one active principle (AP), which comprises a dry powder form:

based on particles comprising at least one active principle (AP), these particles being those described above or those obtained by the process described above;

or obtained from the formulation comprising a suspension in aqueous solution mentioned above.

Advantageously, such a solid pharmaceutical formulation is used for inhalation and pulmonary administration.

According to another of its aspects, the subject matter of the invention is a process for the preparation of medicaments, in particular for parenteral, mucosal, subcutaneous, intramuscular, intradermal, transdermal, intraperitoneal or intracerebral administration or administration into a tumor, indeed even administration by the oral, nasal, pulmonary, vaginal or ocular route, said process consisting essentially in employing at least one of the formulations described above.

BRIEF DESCRIPTION OF THE FIGURES

FIG. 1: in vitro release of IFN-$\alpha$ from formulations comprising particles described in example 2 (white circles), example 3.1 (black triangles), example 3.2 (black diamonds), example 3.3 (black squares), example 4 (black circles) and example 5 (lines).

EXAMPLES

1) Syntheses a) Synthesis of an Anionic Polyelectrolyte Polymer PE1-A Carrying Hydrophobic Groups (Polyglutamate Grafted with $\alpha$-Tocopherol of Synthetic Origin)

15 g of a poly($\alpha$-L-glutamic acid) (with a weight equivalent to approximately 16 900 Da with respect to a polyoxyethylene standard and obtained by polymerization of NCA-GluOMe, followed by hydrolysis, as described in patent application FR-A-2 801 226) are dissolved in 288 ml of dimethylformamide (DMF) while heating at 80° C. until the polymer has dissolved. The solution is cooled to 15° C. and 2.5 g of D,L-$\alpha$-tocopherol (>98%, obtained from Fluka®), dissolved beforehand in 8 ml of DMF, 280 mg of 4-dimethylaminopyridine, dissolved beforehand in 1 ml of DMF, and 1.6 g of diisopropylcarbodiimide, dissolved beforehand in 6 ml of DMF, are successively added. After stirring for 3 hours, the reaction medium is poured into 1200 ml of water comprising 15% of sodium chloride and hydrochloric acid (pH 2). The precipitated polymer is subsequently recovered by filtration and washed with 0.1 N hydrochloric acid, with water and with diisopropyl ether. The polymer is subsequently dried in an oven under vacuum at 40° C. A yield of the order of 90% is obtained. The molar mass, measured by steric exclusion chromatography, is 15 500, with respect to a polyoxyethylene standard. The level of grafted tocopherol, estimated by proton NMR spectroscopy, is 5.1 molar %.

b) Synthesis of an Anionic Polyelectrolyte Polymer PE1-B (Sodium Polyglutamate)

The synthesis of a poly($\alpha$-L-polyglutamic acid) as described in patent application FR-A-2 801 226 is adapted.

The molar mass, measured by steric exclusion chromatography, is 16 900 Da, with respect to a polyoxyethylene standard.

c) Synthesis of a Cationic Polyelectrolyte Polymer PE2-A (Polyglutamate Grafted with $\alpha$-Tocopherol of Synthetic Origin and with Histidinamide)

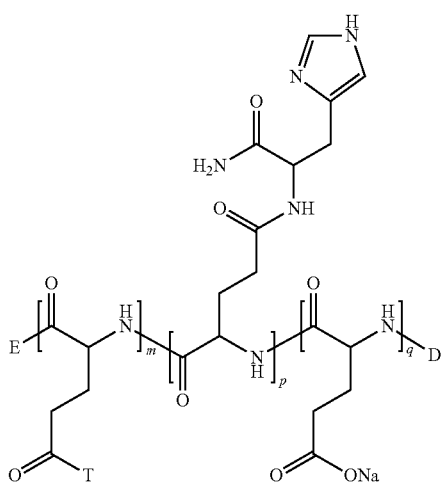

Indices and groups: m=11, p=209, q=0, T=D,L-α-tocopheryl (T)

3 g of a poly(glutamic acid) with a DP of 220 randomly grafted with 5% of racemic α-tocopherol are dissolved by heating at 80° C. in 38 ml of NMP. This solution is cooled to 0° C. and 2.74 g of isobutyl chloroformate and then 2.2 ml of N-methylmorpholine are added. The reaction medium is stirred for 10 minutes while maintaining the temperature at 0° C. At the same time, 8.65 g of histidinamide dihydrochloride are suspended in 108 ml of NMP. 10.6 ml of triethylamine are subsequently added and the suspension obtained is stirred at 20° C. for a few minutes and then cooled to 0° C. The solution of activated polymer is subsequently added to the histidinamide suspension. The reaction medium is stirred at 0° C. for 2 hours and then at 20° C. overnight. 0.62 ml of 35% HCl and then 83 ml of water are subsequently added. The solution obtained is subsequently poured into 500 ml of water at pH 3-4. The solution is subsequently diafiltered against 8 volumes of aqueous saline solution (0.9% NaCl) and 4 volumes of water. The polymer solution is then concentrated to a volume of 300 ml (the polymer concentration is 18 mg/g). The percentage of grafted histidinamide, determined by $^1$H NMR in $D_2O$, is 95%.

d) Synthesis of a Cationic Polyelectrolyte Polymer PE2-B (Polyglutamate Grafted with α-tocopherol of Synthetic Origin and with Arginine)

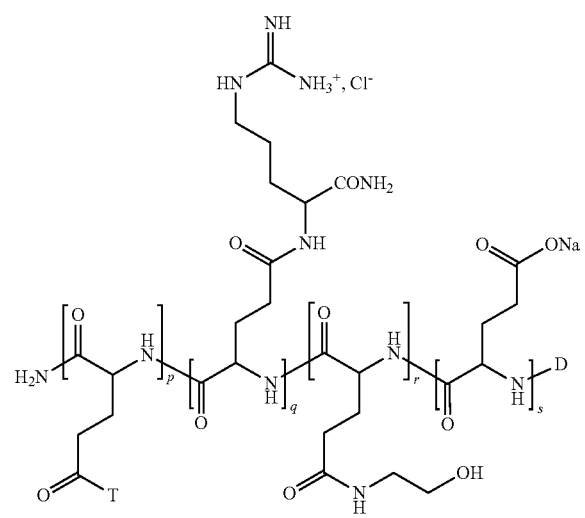

Indices and groups: T=D,L-α-tocopheryl, p=s=11, q=198, r=0

Ten grams of a poly(glutamic acid) with a DP of 220 randomly grafted with 5% of racemic α-tocopherol are dissolved in 125 ml of NMP at 80° C. This solution is cooled to 0° C. and 8.7 ml of isobutyl chloroformate and then 7.35 ml of N-methylmorpholine are added. This reaction mixture is stirred at 0° C. for 15 minutes. At the same time, 24.67 g of argininamide dihydrochloride are suspended in 308 ml of NMP, and 14.7 ml of triethylamine are added. The suspension obtained is stirred at 20° C. for a few minutes and then cooled to 0° C. The milky suspension of activated polymer is then added to this suspension and the reaction mixture is stirred at 0° C. for 2 h and then at 20° C. overnight. After addition of 2.1 ml of a 35% HCl solution and then 100 ml of water, the reaction mixture is run dropwise into 1.6 l of water. The solution obtained is diafiltered against 8 volumes of aqueous saline solution (0.9%) and then 4 volumes of water, and concentrated to a volume of approximately 250 ml. The percentage of grafted argininamide, determined by proton NMR in $D_2O$, is 90%.

e) Synthesis of a Cationic Polyelectrolyte Polymer PE2-C (Polyglutamate Grafted with α-Tocopherol of Synthetic Origin, with Arginine and with Ethanolamine)

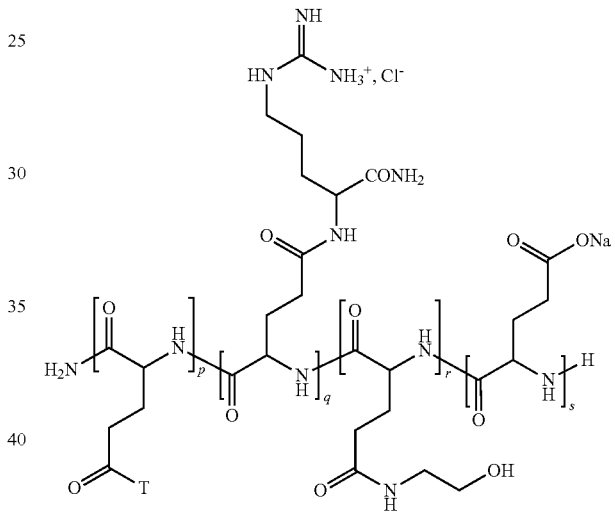

Indices and groups: T=D,L-α-tocopherol, p=11, q=88, r=99, s=22

Ten grams of a poly(glutamic acid) with a DP of 220 randomly grafted with 5% of racemic α-tocopherol are dissolved in 125 ml of NMP at 80° C. This solution is cooled to 0° C. and 9.1 ml of isobutyl chloroformate and then 7.71 ml of N-methylmorpholine are added. This reaction mixture is stirred at 0° C. for 15 minutes. At the same time, 8.2 g of argimiamide dihydrochloride are suspended in 103 ml of NMP, and 9.31 ml of triethylamine are added. 1.6 ml of ethanolamine are further added and the suspension obtained is stirred at 20° C. for a few minutes and then cooled to 0° C. The milky suspension of activated polymer is then added to this suspension and the reaction mixture is stirred at 0° C. for 2 h. 1.2 ml of ethanolamine are added and then the reaction mixture is stirred at 20° C. overnight. After addition of 2.1 ml of a 35% HCl solution and then 200 ml of water, the reaction mixture is run dropwise into 700 ml of water, the pH being adjusted to 7.4. The solution obtained is diafiltered against 8 volumes of aqueous saline solution (0.9%) and then 4 volumes of water, and concentrated to a volume of approximately 250 ml. The percentage of grafted argininamide and grafted ethanolamine, determined by proton NMR in $D_2O$, are respectfully 40 and 45%.

f) Synthesis of a Cationic Polyelectrolyte Polymer Pe2-D (Polyglutamate Grafted with α-Tocopherol of Synthetic Origin, with Arginine and with Ethanolamine)

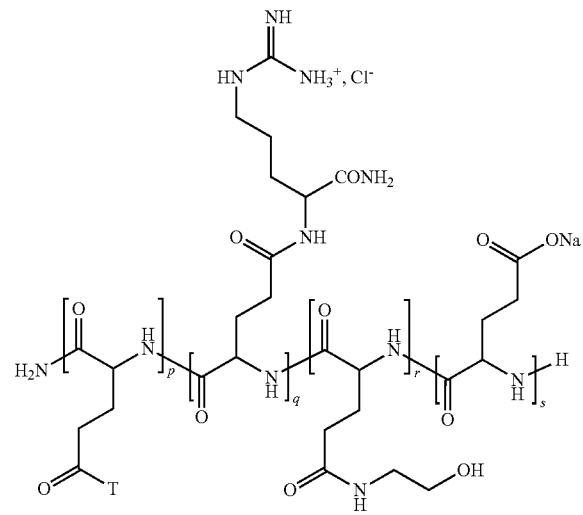

Indices and groups: T=D,L-α-tocopherol, p=11, q=48, r=150, s=11

Ten grams of a poly(glutamic acid) with a DP of 220 randomly grafted with 5% of racemic α-tocopherol are dissolved in 125 ml of NMP at 80° C. This solution is cooled to 0° C. and 8.7 ml of isobutyl chloroformate and then 7.3 ml of N-methylmorpholine are added. This reaction mixture is stirred at 0° C. for 15 minutes. At the same time, 4.61 g of argininamide dihydrochloride are suspended in 58 ml of NMP, and 2.9 ml of triethylamine are added. 2.8 ml of ethanolamine are further added and the suspension obtained is stirred at 20° C. for a few minutes and then cooled to 0° C. The milky suspension of activated polymer is then added to this suspension and the reaction mixture is stirred at 0° C. for 4 h. 1.2 ml of ethanolamine are added and then the reaction mixture is stirred at 20° C. overnight. After addition of 2.1 ml of a 35% HCl solution, the reaction mixture is run dropwise into 730 ml of water, the pH being adjusted to 7.4. The solution obtained is diafiltered against 8 volumes of aqueous saline solution (0.9%) and then 4 volumes of water, and concentrated to a volume of approximately 300 ml. The percentage of grafted argimiamide and grafted ethanolamine, determined by proton NMR in $D_2O$, are respectfully 22 and 68%.

2) Example 1

(Comparative): Preparation of Particles with Polyelectrolytes not Exhibiting a Hydrophobic Group (1) Preparation of a colloidal solution of polymer PE1-B:

The polymer PE1-B obtained according to synthesis b) above is used. This polymer has a half-neutralization pH equal to 5.985.

A colloidal solution of polymer PE1-B is obtained by dissolving it in water, the pH being adjusted to 7.63 by addition of a NaOH solution. The osmolarity of the solution is adjusted to 100 mOsm by introducing the necessary amount of an aqueous NaCl solution. The concentration of polymer PE1-B is adjusted to 8.38 mg/g.

(2) Association of the Protein with the Polymer Pe1-B:

2.4 mg/g concentrated protein IFN-α (PC GEN) is added to the preceding colloidal solution of polymer PE1-B. The association having the following characteristics is obtained:

| [PE1-B] (mg/g) | [IFN-α] (mg/g) | pH |
|---|---|---|
| 4.55 | 1.1 | 7.17 |

The association is produced overnight at 25° C. with stirring.

(3) Preparation of a Colloidal Solution of Poly-L-Arginine (Aldrich P7637):

This polymer has a half-neutralization pH of greater than 9.

A colloidal solution of poly-L-arginine is obtained by dissolving it in water by first adjusting the pH to 0.92 with an HCl solution, then by bringing it back up to pH equal to 6.91 with an NaOH solution and by heating the solution at 45° C. for 15 min. The concentration of polymer poly-L-arginine is adjusted to 5.13 mg/g.

(4) Mixing in Order to Obtain the Particles 1.37 g of the poly-L-arginine solution are added dropwise with stirring at 45° C. to 1.06 g of the IFN-α/PE1-B solution. Stirring is carried out at 45° C. for 15 min. Stirring is then carried out at 4° C. overnight.

The characteristics of the particles obtained are combined in table I below:

The charge ratio Z is the ratio of the number of moles of cationic ionized groups to the number of moles of anionic ionized groups, measured at pHm equal to 6.95.

The size of the particles is measured according to the T Test.

TABLE I

| [polymer] (mg/g) | [IFN-α] (mg/g) | Z | pHm | Size (μm) |
|---|---|---|---|---|
| 4.8 | 0.48 | 1.06 | 6.95 | 15.92 |

(5) Quantification of the Encapsulation of the Protein

The suspension is centrifuged at 8000 rpm for 15 min and the IFN-α in the supernatant is assayed by the method described in the European Pharmacopoeia (colorimetric assaying by UV absorbance).

| Total [IFN-α] (mg/g) | Free [IFN-α] (mg/g) | Yield (%) |
|---|---|---|
| 0.48 | 0.15 | 71 |

Virtually a third of the protein introduced is not encapsulated in the microparticles formed. This proportion cannot result in controlled release.

3) Example 2

Preparation of Particles with a Single Polyelectrolyte (PE1) Exhibiting Hydrophobic Groups (1) Preparation of a Colloidal Solution of Polymer PE1-A:

The polymer PE1-A obtained according to synthesis a) above is used. This polymer has a half-neutralization pH equal to 5.445.

A colloidal solution of polymer PE1-A is obtained by dissolving it in water, the pH being adjusted to 7.53 by addition of a NaOH solution. The osmolarity of the solution is adjusted to 101 mOsm by introducing the necessary amount of an aqueous NaCl solution. The concentration of polymer PE1-B is adjusted to 8.41 mg/g.

(2) Association of the Protein with the Polymer PE1-A:

2.4 mg/g concentrated protein IFN-α is added to the preceding colloidal solution of polymer PE1-A. The association having the following characteristics is obtained:

| [PE1-A] (mg/g) | [IFN-α] (mg/g) | pH |
|---|---|---|
| 4.58 | 1.1 | 7.17 |

The association is produced overnight at 25° C. with stirring.

(3) Preparation of a Colloidal Solution of Poly-L-Arginine (Aldrich P7637):

The solution is prepared in an identical way to that described in example 1.

(4) Mixing in Order to Obtain the Particles 1.24 g of the poly-L-arginine solution are added dropwise with stirring at 45° C. to 1.07 g of the IFN-α/PE1-A solution. Stirring is carried out at 45° C. for 15 min. Stirring is then carried out at 4° C. overnight.

The characteristics of the particles obtained are combined in table II below:

The charge ratio Z is measured at pHm equal to 6.88.

The size of the particles is measured according to the T test.

TABLE II

| [polymer] (mg/g) | [IFN-α] (mg/g) | Z | pHm | Size (μm) |
|---|---|---|---|---|
| 4.7 | 0.505 | 1.00 | 6.88 | 18.24 |

(5) Quantification of the Encapsulation of the Protein

The suspension is centrifuged at 8000 rpm for 15 min and the IFN-α in the supernatant is assayed by the method described in the European Pharmacopoeia (calorimetric assaying by UV absorbance).

| Total [IFN-α] (mg/g) | Free [IFN-α] (mg/g) | Yield (%) |
|---|---|---|
| 0.505 | 0.01 | 98 |

All the protein introduced is encapsulated in the microparticles formed.

4) Example 3

Preparation of Particles Based on PE1-A and on PE2-A, Comprising IFN-α

4.1) Example 3.1

Final Concentration of Polymer Approximately Equal to 10 mg/g, Z being Equal to Approximately 1

(1) Preparation of a Colloidal Solution of Polymer PE1-A:

The polymer PE1-A obtained according to synthesis a) above is used. This polymer has a half-neutralization pH equal to 5.445.

A colloidal solution of polymer PE1-A is obtained by dissolving it in water, the pH being adjusted to 7.45 by addition of a NaOH solution. The osmolarity of the solution is adjusted to 108 mOsm by introducing the necessary amount of an aqueous NaCl solution. The concentration of polymer PE1 is adjusted to 23.88 mg/g.

(2) Association of the Protein with the Polymer PE1-A:

2.4 mg/g concentrated protein IFN-α and 89 mOsm NaCl are added to the preceding colloidal solution of polymer PE1-A. The association having the following characteristics is obtained:

| [PE1-A] (mg/g) | [IFN-α] (mg/g) | pH | Osmolarity (mOsm) |
|---|---|---|---|
| 13.33 | 1.01 | 6.51 | 322 |

The association is produced at 25° C. overnight with stirring. The association is subsequently adjusted to a pH equal to 5.07.

(3) Preparation of a Colloidal Solution of Polymer PE2-A:

The polymer PE2-A obtained according to synthesis c) above is used. This polymer has a half-neutralization pH equal to 6.05.

A colloidal solution of polymer PE2-A is obtained by dissolving it in water, the pH being adjusted to 5.17. The osmolarity of the solution is adjusted to 289 mOsm and the concentration of polymer PE2-A is adjusted to 5.70 mg/g.

(4) Mixing in Order to Obtain the Particles 4.98 g of the PE2-A solution are added dropwise with stirring to 4.61 g of the solution of IFN-α/PE1-A. Stirring is carried out at 4° C. overnight.

The characteristics of the particles obtained are combined in table III below:

The charge ratio Z is measured at pHm equal to 5.17.

The size of the particles is measured according to the T test.

TABLE III

| [polymer] (mg/g) | [IFN-α] (mg/g) | Z | pHm | Osmolarity (mOsm) | Size (μm) |
|---|---|---|---|---|---|
| 9.1 | 0.46 | 0.83 | 5.17 | 370 | 7.7 |

4.2) Example 3.2

Final Concentration of Polymer Equal to 5 Mg/G, Z being Equal to Approximately 10

(1) Preparation of a Colloidal Solution of Polymer PE1-A:

The polymer PE1-A obtained according to synthesis a) above is used.

A colloidal solution of polymer PE1 is obtained by dissolving it in water, the pH being adjusted to 7.52 by addition of an NaOH solution. The osmolarity of the solution is adjusted to 108 mOsm by introducing the necessary amount of an aqueous NaCl solution. The concentration of polymer PE1 is adjusted to 20.21 mg/g.

(2) Association of the Protein with the Polymer PE1-A:

2.4 mg/g concentrated protein IFN-α and 89 mOsm NaCl are added to the preceding colloidal solution of polymer PE1-A. The association having the following characteristics is obtained:

| [PE1-A] (mg/g) | [IFN-α] (mg/g) | pH | Osmolarity (mOsm) |
| --- | --- | --- | --- |
| 1.7 | 0.1 | 5.45 | 324 |

The association is produced at 25° C. overnight with stirring. The association is subsequently adjusted to a pH equal to 4.88.

(3) Preparation of a Colloidal Solution of Polymer PE2-A:

The polymer PE2-A obtained according to synthesis c) above is used.

A colloidal solution of polymer PE2-A is obtained by dissolving it in water, the pH being adjusted to 5.07. The osmolarity of the solution is adjusted to 287 mOsm and the concentration of polymer PE2-A is adjusted to 8.11 mg/g.

(4) Mixing in Order to Obtain the Particles 5.19 g of the PE2-A solution are added dropwise with stirring to 5.02 g of the solution of IFN-αc/PE1-A. Stirring is carried out at 4° C. overnight.

The characteristics of the particles obtained are combined in table IV below:

The charge ratio Z is measured at pHm equal to 4.81.

The size of the particles is measured according to the T test.

TABLE IV

| [polymer] (mg/g) | [IFN-α] (mg/g) | Z | pHm | Osmolarity (mOsm) | Size (μm) |
| --- | --- | --- | --- | --- | --- |
| 5.0 | 0.49 | 13.43 | 4.81 | 306 | 15.1 |

4.3) Example 3.3

Final Concentration of Polymer Equal to 10 mg/g, Z Being Equal to Approximately 10

(1) Preparation of a Colloidal Solution of Polymer PE1-A:

The polymer PE1-A obtained according to synthesis a) above is used.

A colloidal solution of polymer PE1-A is obtained by dissolving it in water, the pH being adjusted to 7.52 by addition of an NaOH solution. The osmolarity of the solution is adjusted to 108 mOsm by introducing the necessary amount of an aqueous NaCl solution. The concentration of polymer PE1-A is adjusted to 20.21 mg/g.

(2) Association of the Protein with the Polymer PE1-A:

2.4 mg/g concentrated protein IFN-α and 89 mOsm NaCl are added to the preceding colloidal solution of polymer PE1-A. The association having the following characteristics is obtained:

| [PE1-A] (mg/g) | [IFN-α] (mg/g) | pH | Osmolarity (mOsm) |
| --- | --- | --- | --- |
| 3.39 | 1.01 | 5.83 | 347 |

The association is produced at 25° C. overnight with stirring. The association is subsequently adjusted to a pH equal to 5.07.

(3) Preparation of a Colloidal Solution of Polymer PE2-A:

The polymer PE2-A obtained according to synthesis c) above is used.

A colloidal solution of polymer PE2-A is obtained by dissolving it in water, the pH being adjusted to 5.08. The osmolarity of the solution is adjusted to 288 mOsm and the concentration of polymer PE2-A is adjusted to 16.37 mg/g.

(4) Mixing in Order to Obtain the Particles 5.25 g of the PE2-A solution are added dropwise with stirring to 5.19 g of the solution of IFN-α/PE1-A. Stirring is carried out at 4° C. overnight.

The characteristics of the particles obtained are combined in table V below:

The charge ratio Z is measured at pHm equal to 4.95.

The size of the particles is measured according to the T test.

TABLE V

| [polymer] (mg/g) | [IFN-α] (mg/g) | Z | pHm | Osmolarity (mOsm) | Size (μm) |
| --- | --- | --- | --- | --- | --- |
| 9.9 | 0.5 | 8.20 | 4.95 | 314 | 10.3 |

5) Example 4

Preparation of Particles Based on PE1-A and on PE2-B, Comprising IFN-α, Final Concentration of Polymer Equal to 5 mg/g, Z=1

(1) Preparation of a Colloidal Solution of Polymer PE1-A:

The polymer PE1-A obtained according to synthesis a) above is used.

A colloidal solution of polymer PE1-A is obtained by dissolving it in water, the pH being adjusted to 7.52 by addition of a NaOH solution. The osmolarity of the solution is adjusted to 108 mOsm by introducing the necessary amount of an aqueous NaCl solution. The concentration of polymer PE1-A is adjusted to 20.21 mg/g.

(2) Association of the Protein with the Polymer PE1-A:

2.4 mg/g concentrated protein IFN-α and 89 mOsm NaCl are added to the preceding colloidal solution of polymer PE1-A. The association having the following characteristics is obtained:

| [PE1-A] (mg/g) | [IFN-α] (mg/g) | pH | Osmolarity (mOsm) |
| --- | --- | --- | --- |
| 3.715 | 1.01 | 5.89 | 335 |

The association is produced at 25° C. overnight with stirring. The association is subsequently adjusted to a pH equal to 6.89.

(3) Preparation of a Colloidal Solution of Polymer PE2-B:

The polymer PE2-B obtained according to synthesis d) above is used. This polymer has a neutralization pH of greater than 9.

A colloidal solution of polymer PE2-B is obtained by dissolving it in water, the pH being adjusted to 6.98. The osmolarity of the solution is adjusted to 288 mOsm and the concentration of polymer PE2-B is adjusted to 6.33 mg/g.

(4) Mixing in Order to Obtain the Particles:

4.06 g of the PE2-B solution are added dropwise with stirring to 4.59 g of the solution of IFN-α/PE1-A. Stirring is carried out at 4° C. overnight.

The characteristics of the particles obtained are combined in table VI below:

The charge ratio Z is measured at pHm equal to 6.85.

The size of the particles is measured according to the T test.

TABLE VI

| [polymer] (mg/g) | [IFN-α] (mg/g) | Z | pHm | Osmolarity (mOsm) | Size (μm) |
|---|---|---|---|---|---|
| 5 | 0.46 | 1.01 | 6.85 | 360 | 17.1 |

6) Example 5

(Comparative) Preparation of Particles Based on PE1-Alone, Comprising IFN-α

The polymer PE1-A obtained according to synthesis a) above is used.

A colloidal solution of polymer PE1-A is obtained by dissolving it in water, the pH being adjusted to 7.52 by addition of a NaOH solution. The osmolarity of the solution is adjusted to 108 mOsm by introducing the necessary amount of an aqueous NaCl solution. The concentration of polymer PE1-A is adjusted to 29.05 mg/g.

2.4 mg/g concentrated protein IFN-α is added to the preceding colloidal solution of polymer PE1. The association is produced at 25° C. overnight with stirring.

The characteristics of the particles obtained are combined in table VII below:

The size of the particles is measured according to the T' test.

TABLE VII

| [PE1-A] (mg/g) | [IFN-α] (mg/g) | pH | Osmolarity (mOsm) | Size (nm) |
|---|---|---|---|---|
| 23 | 0.5 | 7.20 | 300 | 40 |

7) In Vitro Results for Examples 2, 3, 4 and 5

For this, the release of the active principle from the particles according to the invention is measured using the L test.

The release in the L test is shown in FIG. 1 in the form of the percentage of protein released over time.

The formulation of comparative example 2, where only one of the polymers carries hydrophobic groups, exhibits a very weak release profile, with 1.6% of the protein released after 23 hours.

The formulation of comparative example 5, comprising 23 mg/g of particles of PE1, exhibits a similar profile to the particles of example 3.1 (PE1/PE2-A, Z=1 to 10 mg/g) (respectively 93% in 10 hours and 72% in 48 hours).

In the case of the particles of examples 3.2 (PE1/PE2-A, Z=10 and 5 mg/g) and 3.3 (PE1/PE2-A, Z=10 and 10 mg/g), the creation of a constant release flow is observed which is not zero at the end of the experiment: respectively 65 and 19% of the injected protein in 48 hours.

In the case of the particles of example 4 (PE1/PE2-B, Z=1 and 5 mg/g), the creation of a constant release flow is observed which is not zero at the end of the experiment, with the release of 7% of the injected protein in 48 hours.

8) In Vivo Results for Examples 3, 4 and 5

44 rats were separated into 5 groups of 8 or 12 animals and received, in parallel, an immediate-release IR formulation or a prolonged-release formulation corresponding to comparative example 5 or one of the formulations of examples 3 and 4 of the invention, at the dose of 300 μg/kg.

The pharmacokinetic results are combined in table VIII below:

TABLE VIII

| Example | N | $C_{max}$ (ng/ml) | $T_{max}$ median (interval) (hour) | AUC (ng × h/ml) | $T50\%_{AUC}$ (h) | RBA (%) |
|---|---|---|---|---|---|---|
| IFN IR (0.5) | 12 | 100.6 | 05 (0.25-1) | 255.9 | 1.5 | 100 |
| Ex 4 | 8 | 1.8 | 3 (3-6) | 13.6 | 9.0 | 5 |
| Ex 3.1 | 8 | 7.6 | 3 (3-6) | 126.4 | 11.4 | 49 |
| Ex 3.2 | 8 | 6.1 | 3 (3-6) | 128.4 | 18.6 | 50 |
| Ex 3.3 | 8 | 1.7 | 3 (3-12) | 74.2 | 30.7 | >29 |
| Ex 5 | 8 | 3.5 | 12 (6-24) | 95.7 | 18.4 | 62 |

$C_{max}$ represents the mean maximum plasma concentration of protein for all the animals.

$T_{max}$ median represents the median of the time for which the plasma concentration passes through its maximum.

AUC represents the mean area under the curve of the plasma concentration as a function of time.

$T50\%_{AUC}$ represents the mean time at the end of which the area under the curve reaches 50% of its total value.

RBA represents the ratio of the area under the curve of the formulation under consideration to the area under the curve of the IFN IR formulation.

All the formulations exhibit a prolonged-release profile accompanied by a fall in the $C_{max}$ with respect to the IR.

With the exception of the formulation of example 3.1 (PE1/PE2-A, Z=1 to 10 mg/g), the release profile of which is close to that of the formulation of comparative example 5, the terminal slope is lower, which indicates a prolonged residual absorption.

For the formulation of example 3.3 (PE1/PE2-A, Z=10 and 10 mg/g), a release of up to more than one week should be noted.

9) Example 6

Preparation of Particles Based on PE1-A and PE2-C, Comprising IFN-α, Final Concentration of Polymer Equal to 5 mg/g, Z=1

(1) Preparation of a Colloidal Solution of Polymer PE1-A:

The polymer PE1-A obtained according to synthesis a) above is used.

A colloidal solution of polymer PE1-A is obtained by dissolving it in water, the pH being adjusted to 7.15 by addition of a NaOH solution. The osmolarity of the solution is adjusted to 145 mOsm by introducing the necessary amount of an aqueous NaCl solution. The concentration of polymer PE1-A is adjusted to 3.10 mg/g.

(2) Association of the Therapeutic Protein with the Polymer PE1-A:

2.7 mg/g concentrated protein IFN-α: and 89 mOsm NaCl are added to the preceding colloidal solution of polymer PE1-A. The association having the following characteristics is obtained:

| [PE1-A] (mg/g) | [IFN-α] (mg/g) | pH | Osmolarity (mOsm) |
|---|---|---|---|
| 1.94 | 1.01 | 5.6 | 253 |

The association is produced at 25° C. overnight with stirring. The association is subsequently adjusted to a pH equal to 7.0.

(3) Preparation of a Colloidal Solution of Polymer PE2-C:

The polymer PE2-C obtained according to synthesis e) above is used. This polymer has a neutralization pH of greater than 9.

A colloidal solution of polymer PE2-C is obtained by dissolving it in water, the pH being adjusted to 7.04, 288 mOsm and 7.96 mg/g in PBS 140 mOsm.

(4) Mixing in Order to Obtain the Particles:

15.147 g of the PE2-C solution are added dropwise with stirring to 16.374 g of the solution of IFN-α/PE1-A. Stirring is carried out at 4° C. overnight.

The charge ratio Z is measured at pHm equal to 7.

The size of the particles is measured according to the T test.

The characteristics of the particles obtained are combined in the table below:

| [polymer] (mg/g) | [IFN-α] (mg/g) | Z | pHm | Osmolarity (mOsm) | Size (μm) |
|---|---|---|---|---|---|
| 4.9 | 0.49 | 1.0 | 7.02 | 277 | 50.8 |

10) Example 7

Preparation of Particles Based on PE1-A and PE2-D, Comprising IFN-α, Final Concentration of Polymer Equal to 5 mg/g, Z=1

(1) Preparation of a Colloidal Solution of Polymer PE1-A:

The polymer PE1-A obtained according to synthesis a) above is used.

A colloidal solution of polymer PE1-A is obtained by dissolving it in water, the pH being adjusted to 7.02 by addition of a NaOH solution. The osmolarity of the solution is adjusted to 101 mOsm by introducing the necessary amount of an aqueous NaCl solution. The concentration of polymer PE1-A is adjusted to 2.0 mg/g.

(2) Association of the Protein with the Polymer PE1-A:

2.7 mg/g concentrated protein IFN-α and 89 mOsm NaCl are added to the preceding colloidal solution of polymer PE1-A. The association having the following characteristics is obtained:

| [PE1-A] (mg/g) | [IFN-α] (mg/g) | pH | Osmolarity (mOsm) |
|---|---|---|---|
| 1.26 | 1.0 | 5.5 | 234 |

The association is produced at 25° C. overnight with stirring. The association is subsequently adjusted to a pH equal to 7.0.

(3) Preparation of a Colloidal Solution of Polymer PE2-D:

The polymer PE2-D obtained according to synthesis f) above is used. This polymer has a neutralization pH of greater than 9.

A colloidal solution of polymer PE2-D is obtained by dissolving it in water, the pH being adjusted to 7 with HCl 0.1 N or NaOH 0.1 N. The PE2-D polymer concentration is adjusted to 8.82 mg/g.

(4) Mixing in Order to Obtain the Particles:

1.2 g of the PE2-C solution are added dropwise with stirring to 1.2 g of the solution of IFN-α/PE1-A. Stirring is carried out at 4° C. overnight.

The charge ratio Z is measured at pHm equal to 7.

The size of the particles is measured according to the T test.

The characteristics of the particles obtained are combined in the table below:

| [polymer] (mg/g) | [IFN-α] (mg/g) | Z | pHm | Osmolarity (mOsm) | Size (μm) |
|---|---|---|---|---|---|
| 5.0 | 0.48 | 1.0 | 7.1 | 286 | 13.6 |

11) Example 8

(Comparative) Release Speed of Particles Based on PE1-A/PE2-D and on PE1-A/PE2-C Comprising IFN-α

The particles obtained by the preparations described in the above examples 6 and 7 are compared in the L test of continuous flow cell release described above. The following table combined the obtained results:

| | Release (injected protein %) at time | | | |
|---|---|---|---|---|
| | 1 h | 6 h | 12 h | 18 h |
| IFNa/PE1-A/PE2-D Z = 1 5 mg/g | 4.0 | 19.7 | 31 | 39 |
| IFNa/PE1-A/PE2-C Z = 1 5 mg/g | 0.2 | 6.6 | 9.5 | 11.4 |

In conclusion, this example shows that it is possible, particularly selecting a cationic polymer comprising more or less neutral and/or anionic groups, to modulate the AP speed release. Thus, after 12 h, the release is 9.5% for the microparticles obtained from PE2-C and 31% for the microparticles obtained from PE2-D.

The invention claimed is:

1. Particles for the sustained release of at least one active principle (AP), wherein said particles comprise:
    a) a first polyelectrolyte polymer (PE1) in a charged state consisting of an anionic polyamino acid and carrying side hydrophobic groups (GH), wherein said (PE1) spontaneously forms, in water, a colloidal solution of particles when the pHm value is between 3 and 8;
    b) a second polyelectrolyte polymer (PE2) of opposite polarity to the (PE1), wherein said (PE2) forms, in water, a solution or a colloidal solution at said pHm value, wherein (PE2) is neither polylysine nor polyethyleneimine; and
    c) at least one AP associated noncovalently with the particles of the colloidal solution of the (PE1);
    wherein said particles for the sustained release of at least one AP are obtained by mixing, at a pH equal to pHm, the (PE1), in the form of a colloidal solution of particles associated with the AP, with the (PE2), in the form of a solution or colloidal solution.

2. The particles of claim 1, wherein said second polyelectrolyte polymer (PE2) of opposite polarity to the (PE1) carries side hydrophobic groups (GH).

3. The particles of claim 1 or claim 2, wherein the (PE1) and (PE2) are polyamino acids, or pharmaceutically acceptable salts thereof,
   wherein the main chain is formed of residues chosen from the group consisting of aspartic acid residues, glutamic acid residues and combinations thereof; and
   wherein at least one residue comprises at least one hydrophobic group (GH) grafted to at least the (PE1).

4. The particles of claim 3, wherein the polyelectrolyte polymer (PE1) or a pharmaceutically acceptable salt thereof, comprises the following formula (I):

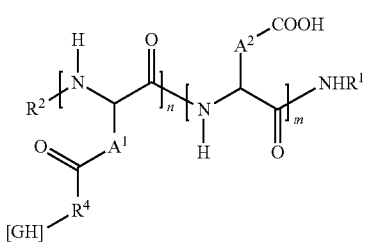

in which:
   $R^1$ is selected from the group consisting of: H, a linear $C_2$ to $C_{10}$ alkyl, branched $C_3$ to $C_{10}$ alkyl, benzyl, —$R^4$-[GH], and a terminal amino acid residue;
   $R^2$ is selected from the group consisting of: H, a linear $C_2$ to $C_{10}$ acyl group, branched $C_3$ to $C_{10}$ acyl group, a pyroglutamate and —$R^4$-[GH];
   $R^4$ represents a direct bond or a "spacer" based on 1 to 4 amino acid residues;
   $A^1$ and $A^2$ independently are —$CH_2$— or —$CH_2$—$CH_2$—;
   n/(n+m) is defined as the molar degree of grafting and its value is sufficiently low for the polymer dissolved in water at pH 7 and at 25° C. to form a colloidal suspension of polymer particles;
   n+m varies from 10 to 1000;
   (GH) represents a hydrophobic group comprising 6 to 30 carbon atoms or is selected from the group of radicals consisting of:
(i) linear or branched $C_1$-$C_{20}$ alkyls, acyls or alkenyls;
(ii) hydrocarbon groups selected from the group consisting of: hydrocarbon groups comprising oxygen, hydrocarbon groups comprising sulfur, hydrocarbon groups with the following formula:

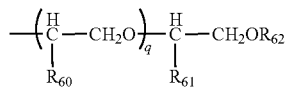

in which:
   $R_{60}$ is a linear or branched $C_1$-$C_{20}$ alkyl, acyl or alkenyl radical,
   $R_{61}$ and $R_{62}$ are identical or different from one another and are hydrogen or a linear or branched $C_1$-$C_{20}$ alkyl, acyl or alkenyl radical,
   q=1 to 100;
(iii) aryls, aralkyls or alkylaryls; and (iv) hydrophobic derivatives selected from the group consisting of: phosphatidylethanolamino, octyloxy-, dodecyloxy-, tetradecyloxy-, hexadecyloxy-, octadecyloxy-, 9-octadecenyloxy-, tocophéryloxy- and cholesteryloxy- groups.

5. The particles of claim 3, wherein the polyelectrolyte polymer (PE2), or a pharmaceutically acceptable salt thereof, comprises the following formula (V):

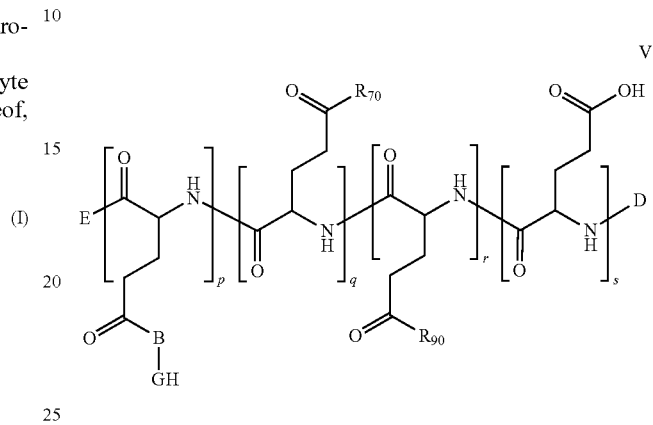

in which:
   E is:
      an —NHR group in which R is selected from the group consisting of: an H, a linear $C_2$ to $C_{10}$ alkyl, branched $C_3$ to $C_{10}$ alkyl and a benzyl;
      a terminal amino acid residue or a terminal amino acid derivative of the following formula:

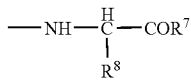

in which:
   $R^7$ is OH, $OR^9$ or $NHR^{10}$
   and $R^8$, $R^9$ and $R^{10}$ independently are selected from the group consisting of H, a linear $C_2$ to $C_{10}$ or branched $C_3$ to $C_{10}$ alkyl, branched $C_3$ to $C_{10}$ alkyl and a benzyl;
   B is a direct bond or a divalent, trivalent or tetravalent bonding group selected from the group consisting of: —O—, —NH—, —N($C_1$ to $C_5$ alkyl)-, a residue of amino acid, diol, triol, diamine, triamine, aminoalcohol and hydroxy acid comprising from 1 to 6 carbon atoms;
   D is selected from the group consisting of: H, a linear $C_2$ to $C_{10}$ acyl group, branched $C_3$ to $C_{10}$ acyl group and a pyroglutamate;
   (GH) represents a hydrophobic group comprising 6 to 30 carbon atoms;
   $R_{70}$ is a pendant cationic group selected from the group consisting of:
      —NH—$(CH_2)_w$—$NH_3^+$ in which w is between 2 and 6,
      —NH—$(CH_2)_4$—NH—C(=NH)—$NH_3^+$,
      —O—$(CH_2)_2$—$NH_3^+$,
      —O—$(CH_2)_2$—$N^+(CH_3)_3$,

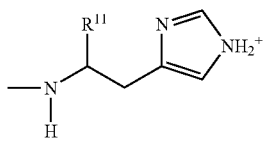

wherein —R¹¹ is selected from the group consisting of: —H, —CO₂H, an alkyl ester, —CH₂OH, —C(=O)—NH₂, —C(=O)—NH—CH₃ and —C(=O)—N(CH₃)₂; and an amino acid residue or an amino acid derivative of the formula:

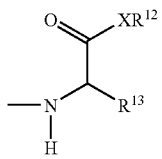

wherein:

X is an oxygen or —NH—,

—R¹² is selected from the group consisting of: H, a linear $C_2$ to $C_{10}$ alkyl, branched $C_3$ to $C_{10}$ alkyl and a benzyl, —R¹³ is selected from the group consisting of: —(CH₂)₄NH₃⁺, —(CH₂)₃—NH—C(=NH)—NH₃⁺, —(CH₂)₃NH₃⁺;

the counteranion of $R_{70}$ is selected from the group consisting of: a chloride, a sulfate, a phosphate and an acetate;

$R_{90}$ is a hydroxyethylamino-, an alkylene glycol residue or a polyoxyalkylene residue;

p, q, r and s are positive integers;

(p)/(p+q+r+s) is defined as the molar degree of grafting of the (GH) and varies from 2 to 99 molar %, provided that each copolymer chain has, on average, at least 3 hydrophobic grafts;

(q)/(p+q+r+s) is defined as the molar degree of grafting of the cationic groups and varies from 1 to 99 molar %;

(p+q+r+s) varies from 10 to 1000;

(r)/(p+q+r+s) varies from 0 to 98 molar %;

(s)/(p+q+r+s) varies from 0 to 98 molar %.

6. The particles of claim 4, wherein $R^4$ is a direct bond.

7. The particles of claim 4, wherein all or a portion of the (GH) are selected independently from the group consisting of: a linear alkoxy or branched alkoxy which comprises from 6 to 30 carbon atoms, an alkoxy which comprises from 6 to 30 carbon atoms and which has one or more annulated carbocycles, and an alkoxyaryl or an aryloxyalkyl of 7 to 30 carbon atoms.

8. The particles of claim 4, wherein the (GH) each represent, independently of one another, a monovalent group of the following formula:

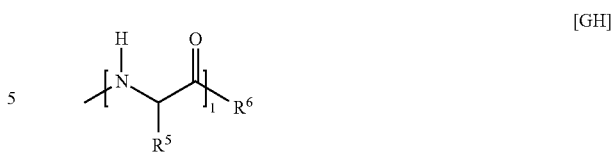

in which:

$R^5$ is selected from the group consisting of: a methyl, isopropyl, isobutyl, sec-butyl and benzyl;

$R^6$ is a hydrophobic group comprising from 6 to 30 carbon atoms; and l varies from 0 to 6.

9. The particles of claim 8, wherein the hydrophobic $R^6$ of the (GH) is selected independently from the group consisting of: a linear or branched alkoxy which comprises from 6 to 30 carbon atoms, an alkoxy which comprises from 6 to 30 carbon atoms and which has one or more annulated carbocycles and an alkoxyaryl or an aryloxyalkyl of 7 to 30 carbon atoms.

10. The particles of claim 4, wherein one of the two polymers (PE1) or (PE2) comprises:

15 to 50 molar % of glutamate monomers;

20 to 55 molar % of nonionizable monomers;

10 to 40 molar % of monomers carrying cationic groups whose half-neutralization pH is greater than 8;

3 to 15 molar % of nonionizable monomers substituted by an hydrophobic group.

11. The particles of claim 4, wherein (PE2) is cationic and simultaneously comprises:

0 to 5 molar % glutamate monomers;

50 to 85 molar % of nonionizable monomers;

10 to 40 molar % of monomers carrying cationic groups who half-neutralization pH is greater than 8; and 3 to 15 molar % of nonionizable monomers substituted by a hydrophobic group.

12. The particles of claim 4, wherein said particles exhibit, at physiological pH, a size, measured in a T test, of between 1 and 100 microns.

13. The particles of claim 4, wherein said particles exhibit, at physiological pH, a bulk density of between 0.15 and 1.1.

14. A process for the preparation of the particles of claim 1 or claim 2 for the sustained release of at least one AP, wherein said process comprises steps of:

1) preparing, at a pHm value between 3 and 8, an aqueous colloidal solution of an anionic polyamino acid (PE1) in a charged state, carrying side (GH), wherein said (PE1) can spontaneously form, in water, a colloidal solution of particles at said pHm value of the pH;

2) adding at least one AP to the (PE1) obtained in step 1, wherein said AP associates noncovalently with the particles of the colloidal solution of said (PE1);

3) preparing a (PE2) of opposite polarity to the first electrolyte polymer (PE1), wherein said (PE2) forms, in water, a solution or a colloidal solution at said pHm value; and 4) mixing, at a pH equal to pHm, the (PE1), in the form of a colloidal solution of particles with which the AP is associated obtained in step 2), with the (PE2), in the form of a solution or colloidal solution obtained in step 3).

15. A pharmaceutical formulation for the sustained release of at least one AP, comprising an aqueous suspension of the particles of claim 1.

16. A pharmaceutical formulation for the sustained release of at least one AP, comprising an aqueous suspension of the particles obtained by a process according to claim 14.

17. A solid pharmaceutical formulation for the sustained release of at least one AP, comprising a dry powder form comprising particles comprising the at least one AP of claim 1.

18. A solid pharmaceutical formulation for the sustained release of at least one AP, comprising a dry powder form comprising particles comprising at least one AP obtained by a process according to claim 14.

19. The particles of claim 7 or claim 9, wherein
  i) the alkoxy which comprises from 6 to 30 carbon atoms,
  ii) the alkoxyaryl which comprises from 6 to 30 carbon atoms and
  iii) the aryloxyalkyl which comprises from 7 to 30 carbon atoms also comprises at least one heteroatom and at least one unsaturation.

* * * * *